United States Patent [19]

Dalrymple et al.

[11] Patent Number: 5,474,451
[45] Date of Patent: Dec. 12, 1995

[54] DENTAL WATER AND AIR PURIFICATION EQUIPMENT

[75] Inventors: Jon Dalrymple, Oakdale; Leslie V. Martens, St. Paul; Jan H. Magnusson, Mahtomedi, all of Minn.

[73] Assignee: Regents of the University of Minnesota, Minneapolis, Minn.

[21] Appl. No.: 190,293

[22] Filed: Feb. 2, 1994

[51] Int. Cl.⁶ .................................................. A61C 1/10
[52] U.S. Cl. ................................................ 433/80; 43/82
[58] Field of Search .................. 433/80, 81, 82, 433/84, 85, 86, 87, 88, 104; 604/85, 150

[56] References Cited

U.S. PATENT DOCUMENTS

| | | | |
|---|---|---|---|
| 2,977,682 | 4/1961 | Flatray | 433/104 |
| 3,364,576 | 1/1968 | Kern, Jr. | 433/104 |
| 4,741,697 | 5/1988 | Herbison | 433/80 |
| 4,941,459 | 7/1990 | Mathur | 433/88 |
| 4,950,159 | 8/1990 | Hansen | 433/80 |
| 4,978,297 | 12/1990 | Vlock | 433/88 |
| 5,165,503 | 11/1992 | Hoffman | 433/104 |
| 5,204,004 | 4/1993 | Johnston et al. | 433/80 |
| 5,370,534 | 12/1994 | Wolf et al. | 433/80 |

*Primary Examiner*—Cary E. O'Connor
*Attorney, Agent, or Firm*—D. L. Tschida

[57] ABSTRACT

Dental hand tools including disposable water and air treatment cartridges. In various constructions, cartridges containing selected arrangements of disinfectant media mount to a detachable, hand tool adaptor manifold or to an integral hand tool manifold. The cartridges purify water and air discharged from the hand tool of undesired microbes and pathogens. Seals at a cartridge body retain the cartridge to the manifold and direct liquid and air flow over external surfaces of the cartridge to an interior cavity containing a halogen disinfectant media (e.g. a multi-valent iodine resin) and/or halogen scavenger media and porous spacers. A retainer may interlock the cartridge to the manifold and means may be included to prevent leaching of the disinfectant by the scavenger media. Various constructions of handpieces, syringes and scalers compatible with alternative adaptors or having integral cartridge manifolds are disclosed. Spray tips with integral manifolds and detachable cartridge manifolds which align to water and air discharge ports are also disclosed.

33 Claims, 22 Drawing Sheets

DENTAL WATER AND AIR PURIFICATION EQUIPMENT

BACKGROUND OF THE INVENTION

The present invention relates to dental air and water line purification assemblies and, in particular, to manifold assemblies which support disposable disinfectant cartridges to a variety of dental hand tools, such as air-powered, high speed handpieces, air-water syringes and scalers. Alternative constructions integrate the cartridge manifolds into hand tool adaptors, hand tool handles or discharge tips.

The presence of microorganisms within dental unit water lines (DUWL) has been documented in medical and dental literature and discussed at related symposia. Studies have confirmed the presence of varieties of bacterium, viruses and protozoa at nutrient rich biofilms that form over time on the tubing walls of the water supply lines that feed hand tools of dental and medical practitioners. Biofilms also exist within the flow channels of the hand tools. Such microorganisms can include non-pathogenic microbes, as well as pathogenic microbes.

The microbes can be admitted to the water lines and hand tools from municipal water supplies and the patients being treated. The later contamination occurs with backflow conditions that exist during typical patient treatments and the use of conventional hand tools. Backflow or passive retraction arises for a variety of reasons such as laminar flow, eddy currents, vortexes, and venturi effects within the hand tool and associated tubings which draw microorganisms that are present in the moisture laden working space into the water and air lines.

Although most practitioners commonly employ procedures to periodically flush the water lines at the start of a week, with the beginning of each day, and/or between patients, the involved fluid mechanics principally remove only loosely attached microbes which may form between flushings. During normal use, a laminar flow at the walls, otherwise, provides a stationary flow condition, which does not particularly affect the growing microbes. Microbe concentrations of $1 \times 10^7$ per ml have been observed in sampled water from DUWL's.

Decontamination efforts directed to minimize and contain the potential health risks represented by microbial colonies dwelling in most DUWL's have included attempts to flush chemical disinfectants through the DUWL; sterilize selected hand tool components (e.g. by autoclaving), including the DUWL; mount anti-retraction systems or check valves into the DUWL to prevent backflow; and use unit dose, sterilized and/or distilled water or saline packs with each patient.

The problem and some of the foregoing attempts to find solutions to contain the problem are discussed in the following articles: "Dental Unit Water Lines", K. Scarbeck, *AGD Impact*, pp. 3, 6–12, November, 1993; "Microbial Contamination of Dental Unit Water Lines-Prevalence," Intensity and Microbiological Characteristics", JF. Williams et al, *JADA*, Vol. 124, pp. 5–65 (October 1993); "Expanding the Bubble", L. H. Meskin, *JADA*, Vol. 124, pp. 9–12 (October 1993); and "Dental Unit Water Lines Under Review—ADA Workshop Looking at Ways to Limit Bacterial Presence", J. Jakush, *ADA News*, pp. 14, 15 (Sep. 20, 1993).

NASA has considered the problem with respect to space travel. Various commercial vendors of water treatment chemicals also provide different assemblies and packaging arrangements of disinfectants to treat water at the point of entry to a building or water supply fixture.

Water purification assemblies for single and multi-patient treatment stations are also known. Such assemblies are sold by Ecomaster Corporation, St. Paul, Minn. and include cartridge based filtration materials and multi-valent iodine resin bactericides and virucides for purifying relatively large volumes of water supplied to medical and dental treatment stations. Although the latter assemblies minimize contaminants introduced from a water supply source, microbial growth and biofilms can still exist in the conduits intermediate the treatment assembly and the hand tools contacting the patient.

Various devices are also known which mount to the tubing sections of the DUWL. U.S. Pat. No. 5,204,004 discloses a microporous membrane filter and assembly for retaining a microbe filter to the DUWL tubing. U.S. Pat. No. 5,230,624 discloses an iodinated cartridge that includes a single bed of disinfectant media and couples to the DUWL tubing to admit a residual amount of disinfectant to liquid passing through the tubing.

In appreciation of the foregoing problems and limitations of existing water and air disinfectant devices, the present invention provides alternative mechanisms for treating or purifying the water and air that contacts a dental or medical patient directly at a discharge port of a hand tool or as close as physically possible to the discharge port. The viability of such treatment devices has been confirmed in studies of water periodically sampled from hand tools equipped with the invention.

SUMMARY OF THE INVENTION

It is accordingly a primary object of the invention to provide a means for purifying liquids and air distributed to dental and medical patients directly at or closely adjacent to the water and air discharge ports of a hand tool.

It is a further object of the invention to provide mechanisms including disposable cartridges which contain one or more beds of halogen disinfectant media and/or halogen scavenger media that are selected and arranged to devitalize undesired microbes, especially, pathogenic bacterium, viruses and protozoa, and remove residuals of the disinfectant media.

It is a further object of the invention to provide manifold assemblies which are compatible with conventional handle sections of dental hand tools, for example, high speed handpieces, scalers and air-water syringes.

It is a further object of the invention to provide manifold assemblies which are compatible with the dispensing tips of air-water syringes.

It is a further object of the invention to provide manifold constructions which segregate air and water flow at the discharge ports of a hand tool.

It is a further object of the invention to provide an adaptor manifold which accepts single use unit dose disposable cartridges (i.e. replaced after treatment of each patient), and which mounts to a variety of conventional dental and medical hand tools to purify delivered air and water.

It is a further object of the invention to provide hand tools including integral, cartridge receiving manifolds.

It is a further object of the invention to provide unit dose cartridge constructions which cooperate with the manifold to interrupt air and/or liquid flow conduits to redirect liquid and air flow through an internal cartridge column containing one or more beds of disinfectant media, halogen scavengers, filtrates and/or intervening porous spacers.

It is a further object to provide means for retaining the disinfectant cartridge to the manifold.

It is a further object to provide means for preventing leeching of the disinfectant media by an included scavenger media.

Variations of the foregoing objects, advantages and distinctions of the invention are achieved in alternative adaptor constructions which thread mount to a hand tool handle. The adaptors provide a disposable, unit dose cartridge receiving manifold that interrupts a liquid and/or air flow conduit to or within a dental hand tool. Seals at the cartridge cooperate with the manifold to re-direct flow along exterior surfaces of the cartridge to inlet ports to an internal flow column. One or more beds of halogen disinfectant, halogen scavenger media and intervening porous spacers contained within the cartridge purify the discharged liquid and/or air. The media assures a supply of air and liquids free of undesired microbes, pathogens and disinfectant residuals and can prevent reverse migration of microbes into the DUWL. In combination with periodic hand tool sterilization, disease transmission is controlled.

Alternative constructions of disposable, unit dose cartridges are also disclosed. In a preferred cartridge construction, the disinfectant and/or scavenger media and porous spacers coaxially mount within the cartridge housing. The cartridge may also include means to prevent leeching of the disinfectant by the scavenger media. In another construction, liquid flow is directed through annularly arranged beds of disinfectant and halogen scavenger media to a center bore. In still another cartridge, multiple columns containing separate arrangements of air and water treatment media are provided. Surfaces of the cartridge are formed to mate and cooperate with the manifold to confine and direct water and air flow and retain the cartridge to the manifold.

In various hand tool constructions, cartridge receiving manifolds are formed into the handles of dental hand tools. Exemplary high speed handpieces, scalers and air-water syringes are disclosed. The cartridges are alternatively supported at acute angular displacements to a longitudinal handle axis and contained conduits or in coaxial alignment to provided water and air conduits.

In still other constructions, modified air and water discharge tip pieces and detachable cartridge receiving tip manifolds are provided for air-water syringes. Variations of the tip manifolds alternatively provide a cartridge manifold intermediate a detachable tip section and a syringe handle, within the body of a unitary tip piece or directly at the air-water discharge ports of the tip piece. Sealed and isolated air and water supply conduits are formed upon securing the cartridge to the manifold.

Still other objects, advantages and distinctions of the invention are more apparent from the following description of various assemblies depicted in the appended drawings. To the extent various modifications and improvements have been considered, they are described as appropriate. The description should not be strictly construed in limitation of the invention. Rather, the scope of the invention should be interpreted in view of the appended claims.

DESCRIPTION OF THE PREFERRED EMBODIMENT

With attention to FIGS. 1 through 6, views are shown of a presently preferred adaptor assembly 2 and disinfectant cartridges 50 and 100 which mount to the adaptor 2. The adaptor 2 finds application with a variety of dental hand tools. In various forms, the adaptor 2 has been integrated into air driven handpieces, reference FIGS. 1, 7 and 8; air driven sonic scalers, reference FIGS. 9, 10 and 11; and air-water syringes, reference FIGS. 11 through 16. Dual, air and water treatment, adaptor and hand tool constructions are shown at FIGS. 18 through 22. The details of such adaptor, hand tool and further cartridge constructions are described below with respect to the related drawings.

Figure 1:
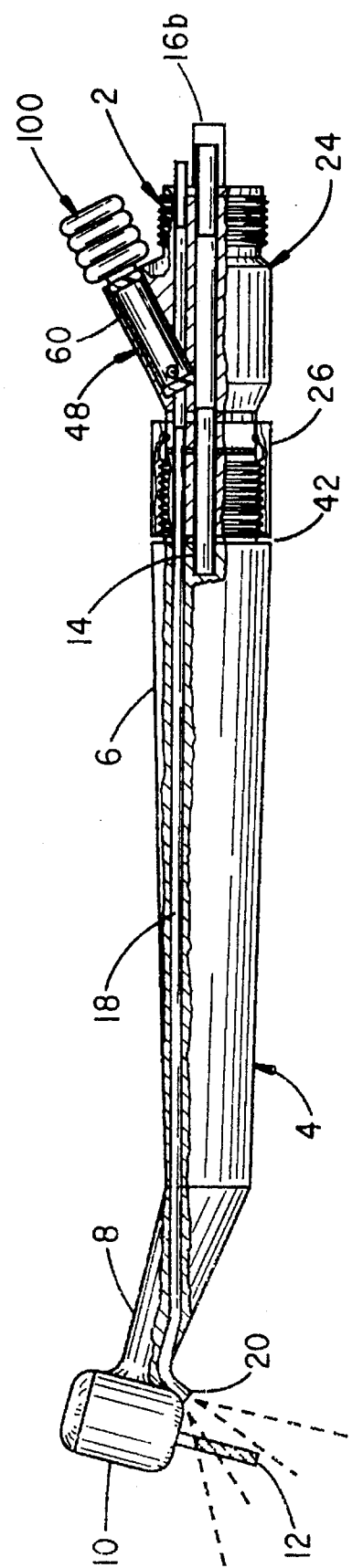
FIG. 1 is a longitudinal cross section view through a high speed dental handpiece and attached adaptor of the invention which includes a disinfectant cartridge.
Figure 2:
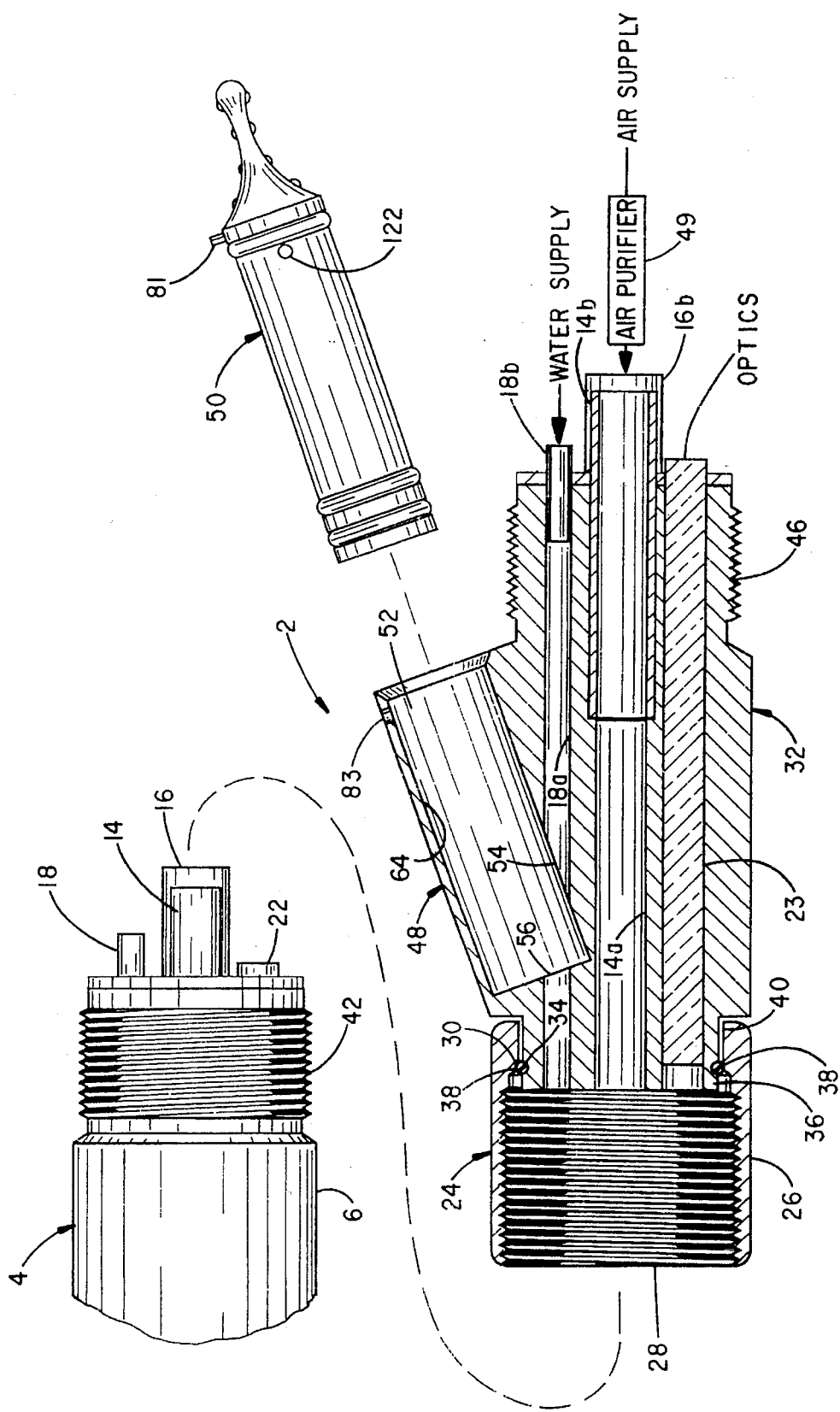
FIG. 2 is a plan view shown in exploded assembly of the adaptor of FIG. 1 and a preferred disinfectant cartridge.
Figure 3:
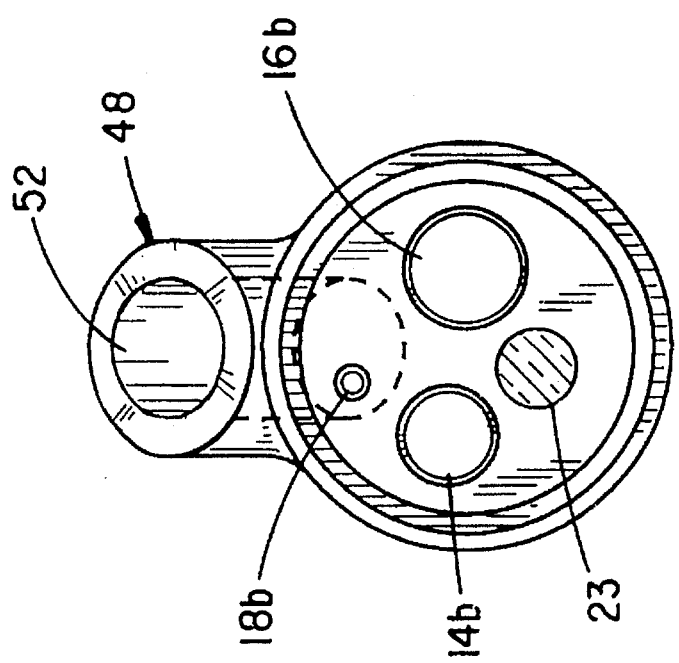
FIG. 3 is an end view of the adaptor of FIG. 2.

As regards air driven dental handpieces, a variety of types and styles of handpieces or drills 4 are commercially available, FIGS. 1, 2 and 3 depict one common style. The handpiece 4 generally provides a shaped handle 6, which is configured to facilitate manipulation by a dentist within the confined space of a patient's mouth. Extending from a neck 8 of the handle 6 is a head or chuck 10 which supports a suitable burr 12. A supply of pressurized drive air is provided to the handle 6 and an internal conduit 14 from an air source and hosing (not shown).

The conduit 14 extends through the handle 6 to the head 10 and powers a rotary drive assembly (not shown) at a suitable speed in relation to the regulated air source to operate the burr 12 and shape desired surfaces of a tooth, remove decay, etc.. An exhaust air conduit 16, which is typically sized to a slightly larger diameter than the drive air conduit 14, receives and conveys the exhaust air from the drive assembly through the handpiece 4 and away from the patient. For some hand tools, exhaust air may be partially discharged at the head 10.

Also extending within the handpiece 4 is a coolant conduit 18 and through which water is typically conducted. A liquid outlet or discharge port 20 is positioned adjacent the tooth and burr 12 and from which a pressurized spray is emitted to cool the tooth and burr 12 and permit a degree of rinsing of debris which collects in the vicinity of the tooth under repair.

Depending upon the complexity of the handpiece 4, additional conduits or members may extend within the handle 4, such as an optical fiber 22, reference FIG. 2. The fiber 22 is commonly used in various handpieces to conduct light and provide additional illumination to the work area, beyond the reflected background light and room light.

The handpiece 4 is typically formed from chrome plated brass, stainless steel or other suitable materials. The handpiece 4 and many of the other hand tools discussed below are constructed to withstand repeated cleanings and sterilizations, such as by steam autoclaving. The latter cleanings are typically performed on a periodic basis established by the practitioner. Preferably, such cleanings occur after each patient, although may occur semi-weekly or weekly. If performed after each patient, preferably any microbial contamination within the hand tool is sterilized and subsequent microbe transmission concerns need only be directed to the air and liquids discharged from the hand tool.

Where a practitioner does not sterilize each hand tool for each patient, the practitioner typically flushes at least the coolant conduit 18 in between patients. Recommended standards established by the American Dental Association are set out in a publication entitled *Recommended Infection Control Practices For Dentistry* (1993).

Because a non-sterile coolant water is typically provided at the conduit 18, over time, a biofilm typically develops along the interior surfaces of the conduit 18 and the supply water lines to the handpiece 4. Varieties of pathogenic and non-pathogenic microbes, which are collectively referred to below as microbes or microorganisms, may include among other contaminants, pathogenic and non-pathogenic bacterium, viruses and protozoa. The microbes commonly found in such biofilms are admitted with the supply water and may also migrate into the handpiece 4 from the patient via the discharge port 20. Such migration can occur due to the rather moist, humid environment of the work area, equipment contact with the patient's mouth or saliva or normal prolonged exposure of the port 20 to room air. Some of the documented types of microbes are discussed in the earlier referenced papers. It is these microbes that can be transmitted to a broad range of individuals through the normal day to day activities of a dentist or physician.

In appreciation of the foregoing health hazards and to provide a mechanism for treating air and water from dental hand tools, the handpiece 4 includes a disinfectant containing treatment adaptor 2. The adaptor 2 is shown in longitudinal cross section at FIG. 2 and in end view at FIG. 3. The adaptor 2 is secured to the handpiece 4 with a coupler 24. The coupler 24 comprises a threaded sleeve or nut 26 which has a center bore 28 that contains a split, snap ring 30. A body piece 32 contains a number of bores 14a, 18a, and an exhaust air bore (not shown), which mate to portions of conduits 14, 16 and 18, and an optical fiber 22 that extend from the aft end of the handle 6. The extensions of the conduits 14, 16 and 18 mount within the bores 14a, 18a and the bore which mates with the exhaust conduit 16. Tubular, stub or extension pieces 14b, 16b and 18b project from the inlet end of the adaptor 2. The optical fiber 22 abuts a section of optical fiber 23 at the adaptor 2.

The nut 26 is retained to the body 22 with the snap ring 30 in a double capture arrangement. That is, the snap ring 30 first mates with an annular groove 34 in a fore-end 36 of the body 32. Once the snap ring 30 is seated, the fore end 36 is retracted slightly to cause the snap ring 30 to seat within a second annular groove 38, which is provided in a bore 40 of the nut 26.

The nut 26, in turn, is secured to the handle 6 at a threaded surface 42, after aligning the conduits 14, 14a; 16, 18, 18a; and fibers 22, 23. The nut 26 is then free to rotate without conflicting with the various conduits and fibers.

Figure 12:
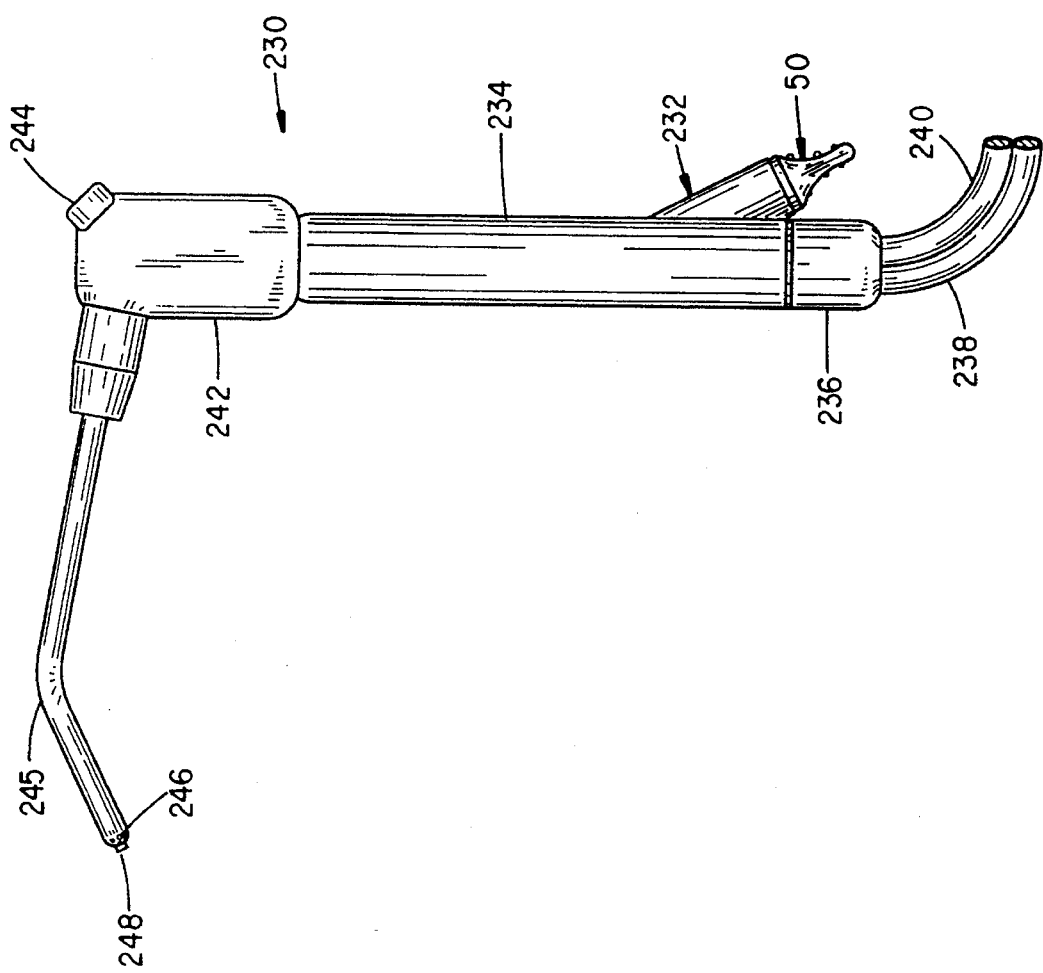
FIG. 12 is a plan view of an air-water syringe including an integral disinfectant cartridge manifold.

A similar mounting arrangement is provided at a threaded coupler (not shown) that is secured to the air, water and optical supply lines which mount to the inlet end of the adaptor 2. An exemplary coupler 236 of this type is shown at FIG. 12. The coupler mounts to a threaded surface 46 at the inlet end of the body 32. The supply lines are typically contained in a single tubular flexible cover, although may separately attach to the coupler in the manner of FIG. 12. The supply lines provide the necessary regulated air and water to the hand tool.

A manifold 48 projects from the adaptor body 32 and receives a disinfectant cartridge 50 at a bore space 52. The bore space 52 interrupts the coolant bore 18a at an inlet port 54 and an outlet port 56. The cartridge 50 is typically constructed in a unit dose, disposable form and mounts within the bore space 52. The cartridge 50 is typically replaced after each patient treatment to assure a sufficient supply of disinfected and purified water to each patient. Coolant water is directed into the manifold 48 from the port 54, through the cartridge 50, to the outlet port 56, and to the handpiece 4.

Before the water is admitted to the handpiece 4, one or more beds of disinfectant media contained within the cartridge 50 treats the water to devitalize substantially all microbial contaminants and contained in the coolant water. Residual disinfectant in the water is also typically removed. However, depending upon the cartridge construction, if a residual of the disinfectant media is permitted, the residual also treats any biofilm resident in the conduit 18. For the cartridge 50, such residuals are normally removed in preference to frequent autoclavings of the hand tool.

Figure 17:
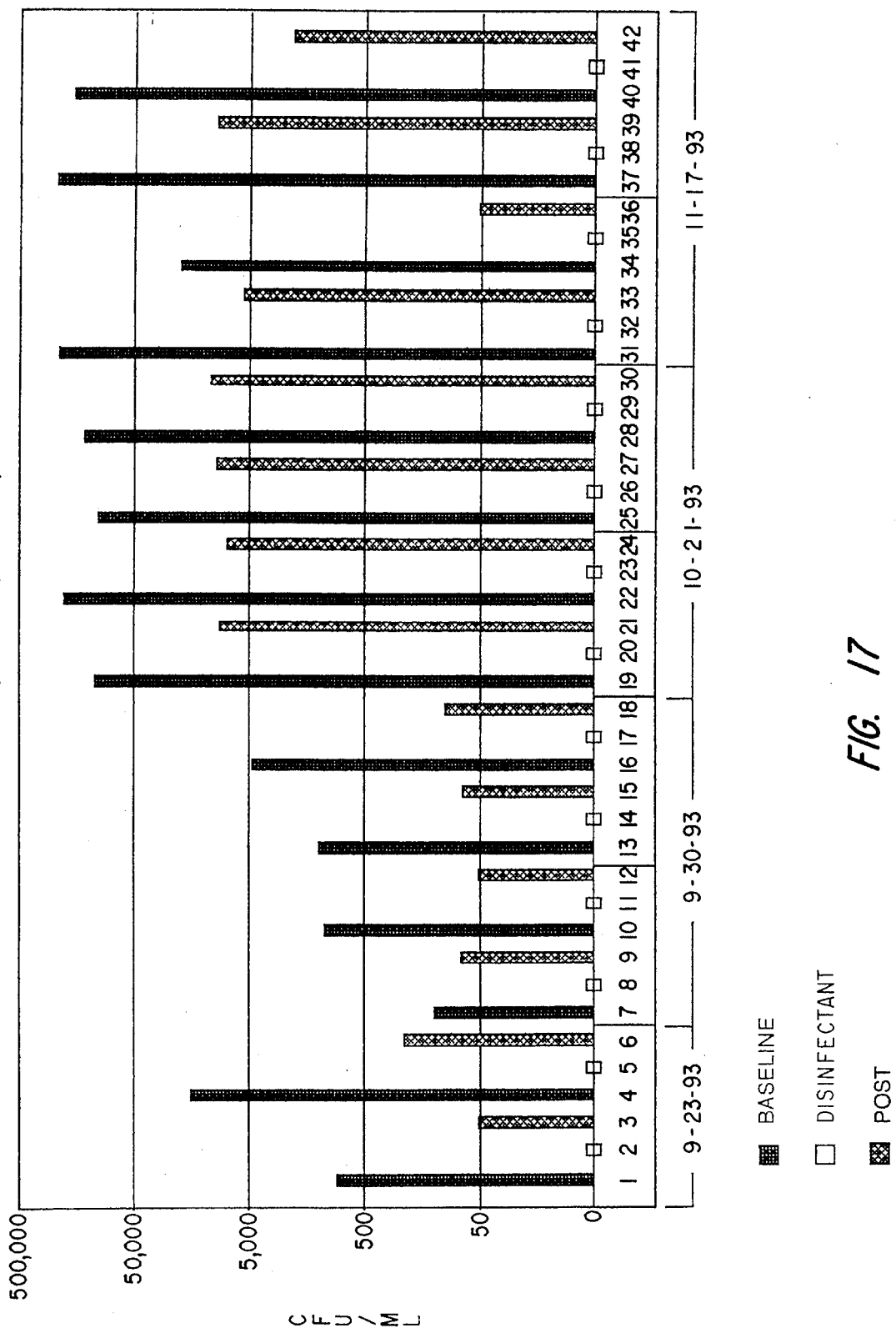
FIG. 17 is a bar chart of test data, comparing the water samples taken from various hand tools with and without the benefit of the invention.

With continued use and normal cleaning of the handpiece 4, sample testing, reference FIG. 17, has demonstrated that the water supplied from the cartridge 50 is substantially free of all microbial contaminants. The potential contamination and transmission of disease to a dentist's or physician's patient population is thereby reduced.

With reference to FIG. 17, a bar graph of comparative samples taken from hand tools adapted to include the disinfectant cartridges of the invention are shown. Samples were taken before and after mounting cartridges to each hand tool on a number of different days. Various samples were permitted additional incubation time to confirm the effectiveness of the invention. The samples 2, 5, 8, 11, 14, 17, 20, 23, 26, 29, 32, 35, 38 and 41, were taken from hand tools containing a disinfectant cartridge, and as depicted no bacterial growth was observed. Thus demonstrating the efficacy of the invention to purify the discharged water of undesired microbes.

Other relevant notes to FIG. 17 are that the samples 1, 3, 7–9, 13–15, 19–21, and 25–27 were taken for air/water syringes and all others were taken for high speed handpieces. The samples 13–18 are the same as the samples 7–12, but incubated an additional 14 days; and the samples 25–30 are the same as the samples 19–24, but incubated an additional 5 days.

Appreciating that many airborne microbes may also contaminate the handpiece 4, an air purifier 49 may be fitted to the air lines which supply the handpiece 4. The purifier 49 removes microbes from the air supplied to the head. Although the exhaust air is normally conducted away from the handpiece 4, leakage commonly occurs at the head; and thus a desire to also protect a patient from airborne microbes. Alternatively, an air purifier may be fitted within the adaptor 2 or within the handpiece 4. Depending upon dimensional tolerances, FIGS. 18 through 22 show exemplary constructions of adaptors and hand tools which have been converted to contain multiple or duplex disinfectant cartridges. Such cartridges interrupt the water and air conduits.

Figure 18:
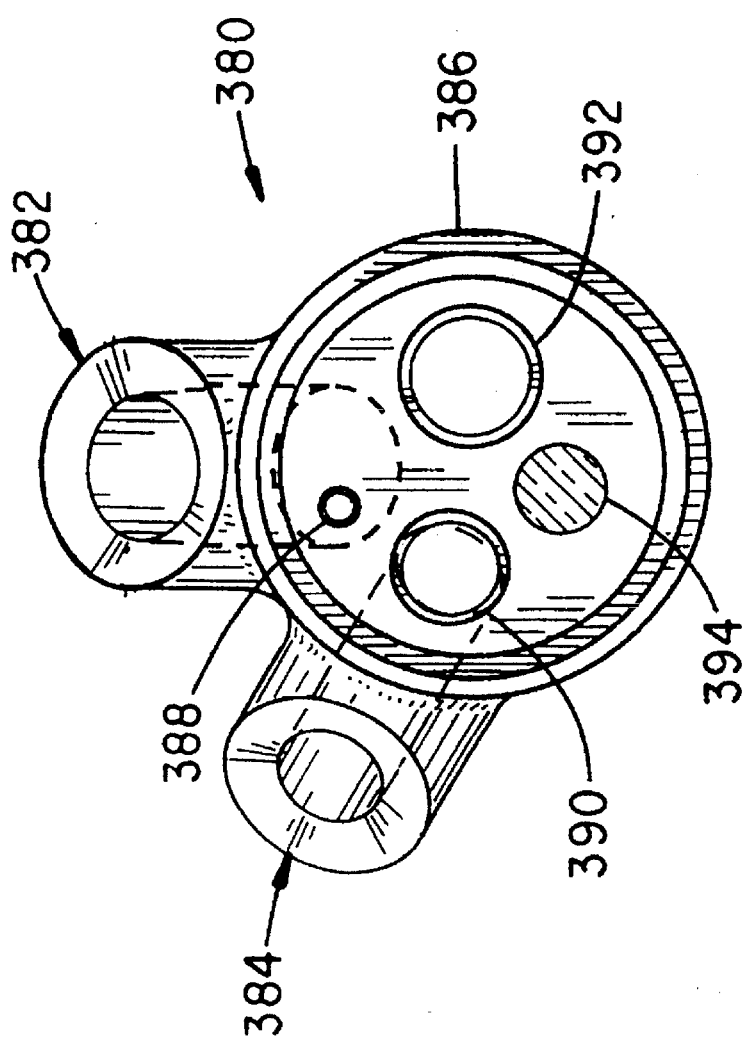
FIG. 18 is an end view of an adaptor similar to that of FIGS. 1–3 having separate air and water disinfectant cartridge manifolds.
Figure 19:
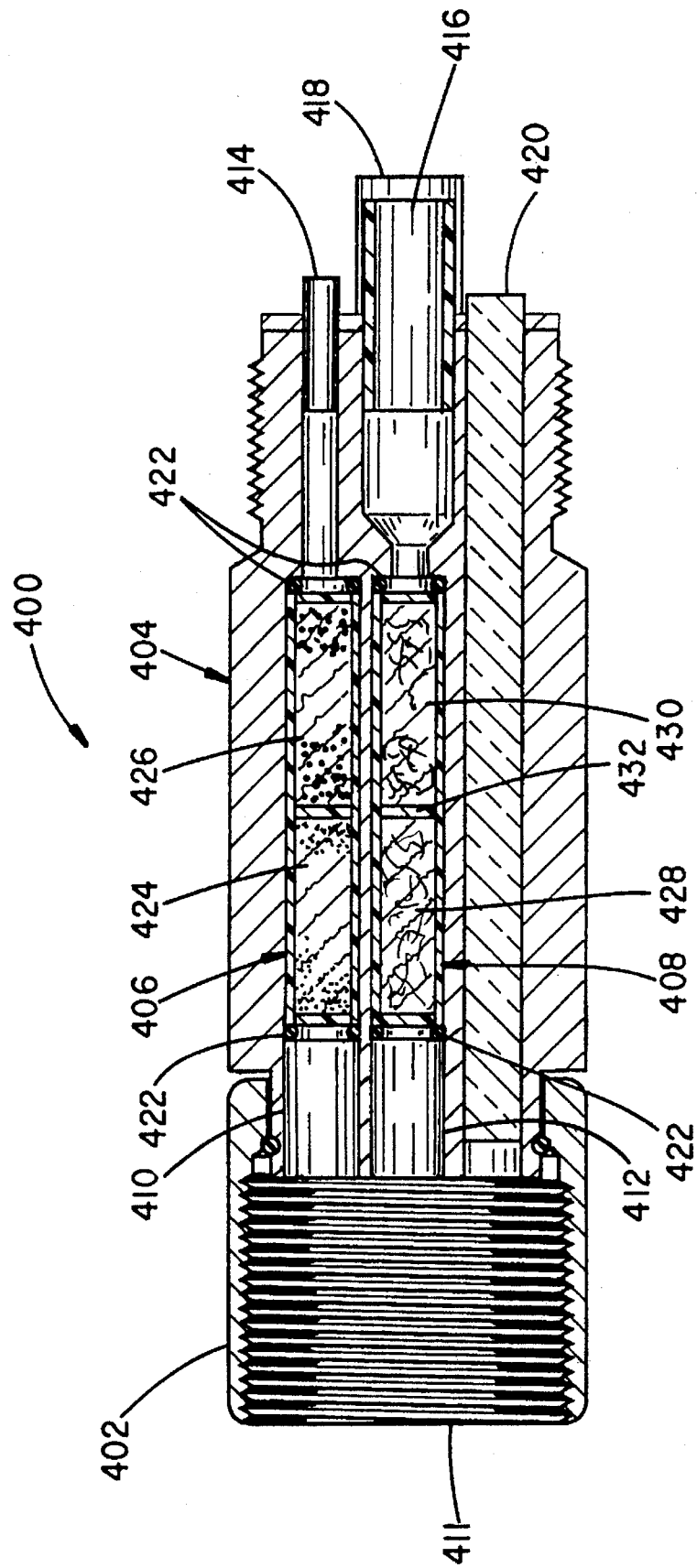
FIG. 19 is a longitudinal cross section view through an adaptor manifold having separate, coaxially arranged air and water disinfectant cartridges.
Figure 20:
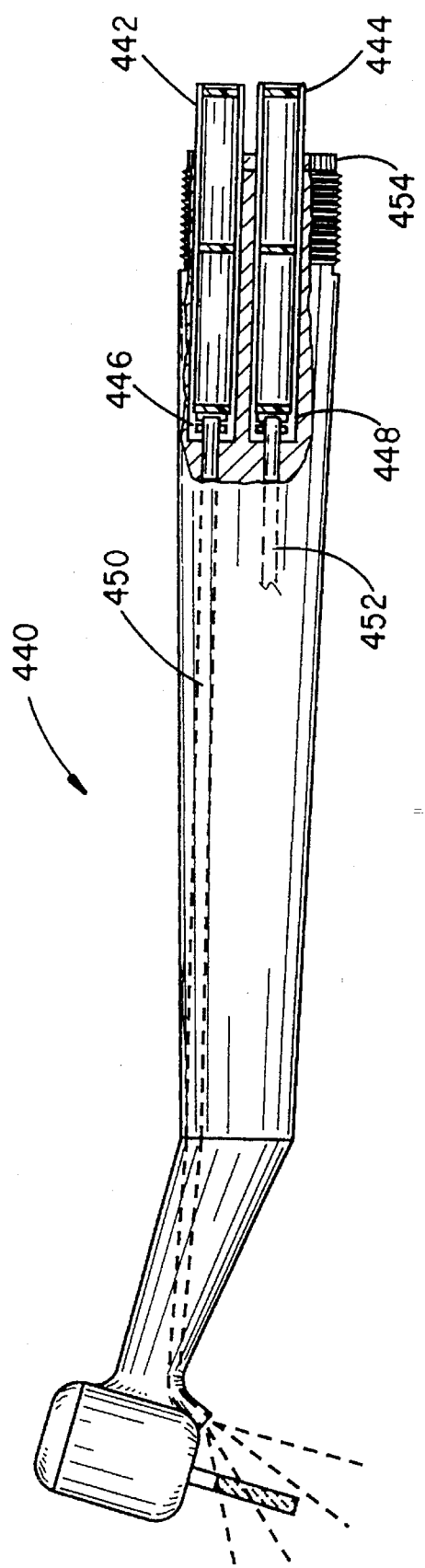
FIG. 20 is a plan view shown in partial longitudinal cross section view through a handpiece including separate, coaxial air and water disinfectant cartridges.
Figure 21:
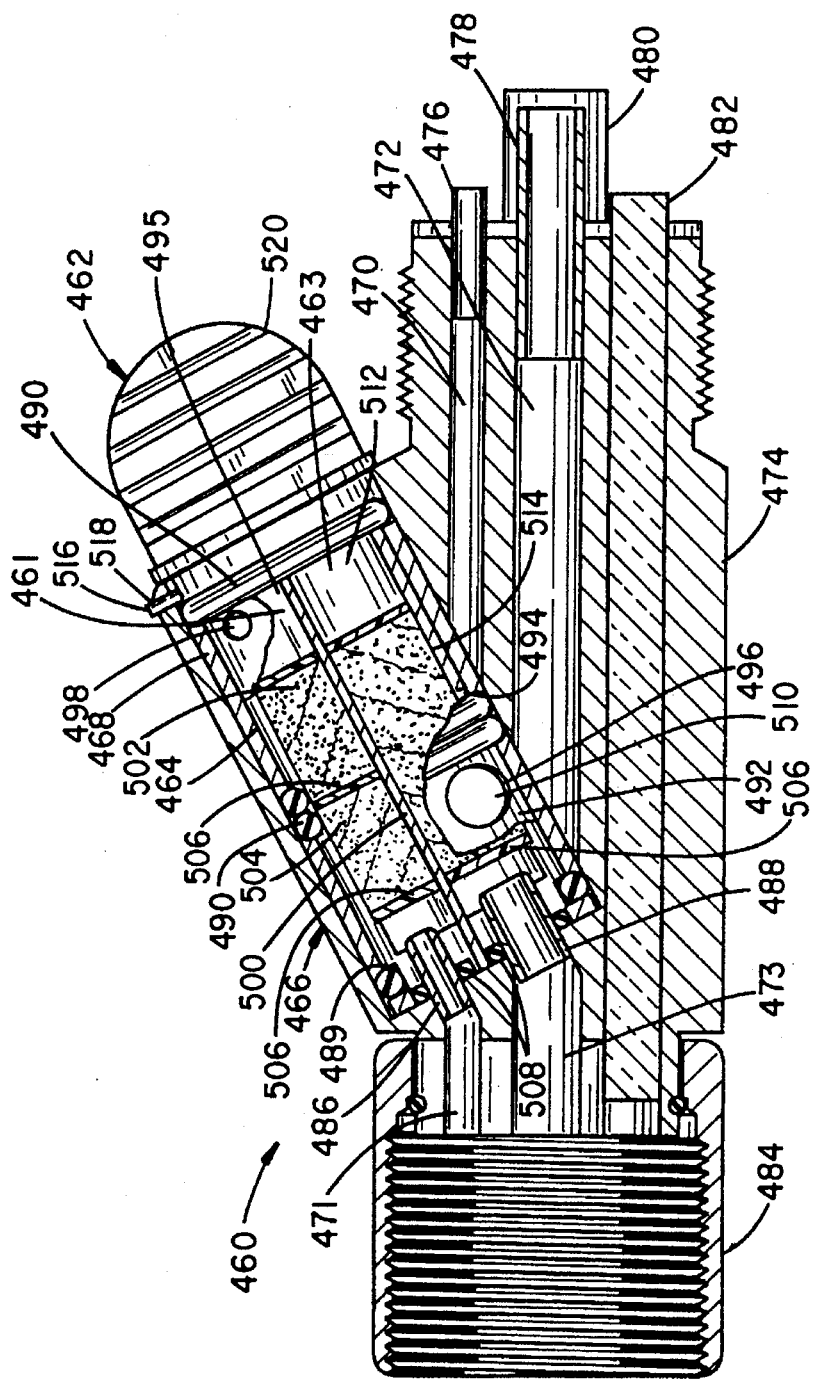
FIG. 21 is a longitudinal cross section view through an adaptor manifold similar to FIGS. 1–3 containing a disinfectant cartridge having separate air and water treatment columns.
Figure 22:
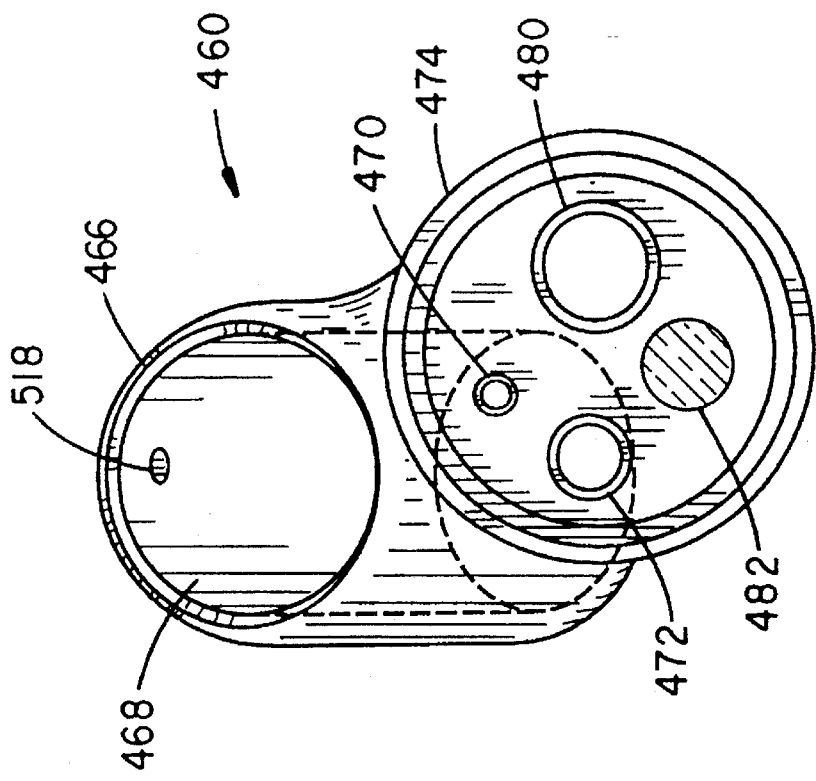
FIG. 22 is an end view of the adaptor of FIG. 21.

The air and water flows are at the assemblies of FIGS. 18 through 20 are particularly segregated to separate cartridges containing beds of disinfectant media. FIGS. 21 and 22 show an adaptor 460 that supports a single duplex cartridge 462. The cartridge 462 contains separate, flow columns which support preferred beds of disinfectant media.

Figure 4:
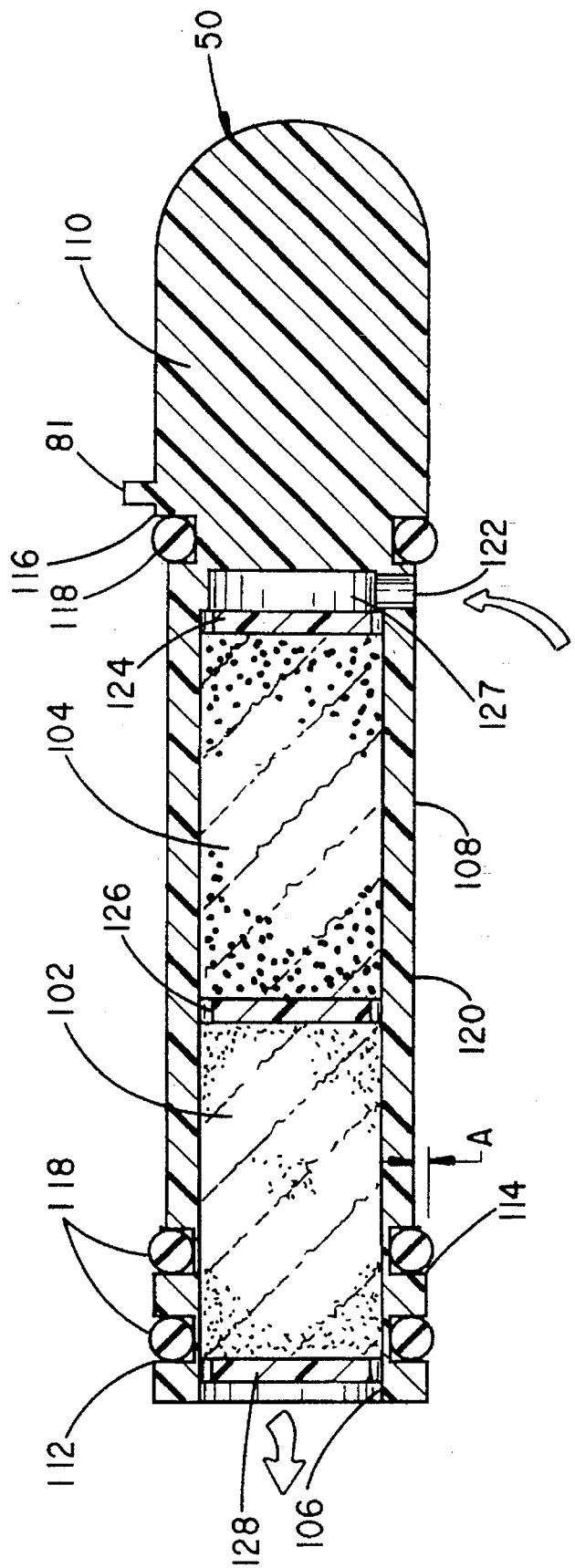
FIG. 4 is a longitudinal cross section view through a the cartridge of FIG. 2.
Figure 5:
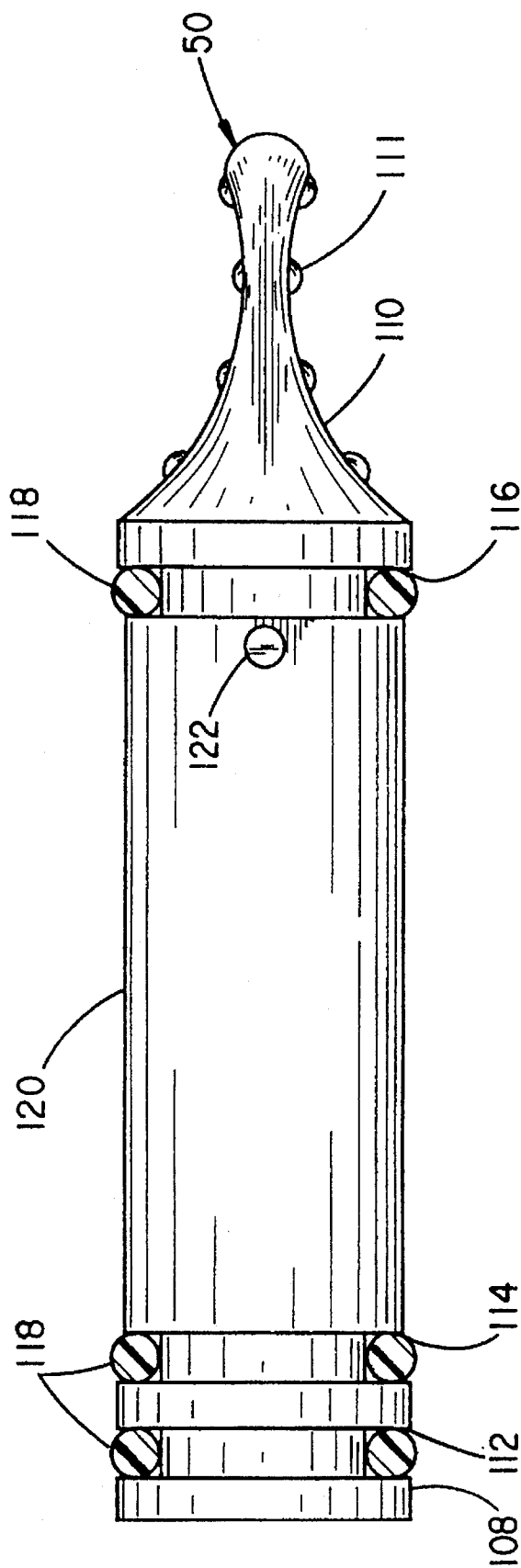
FIG. 5 is a plan view of the cartridge of FIG. 2.
Figure 6:
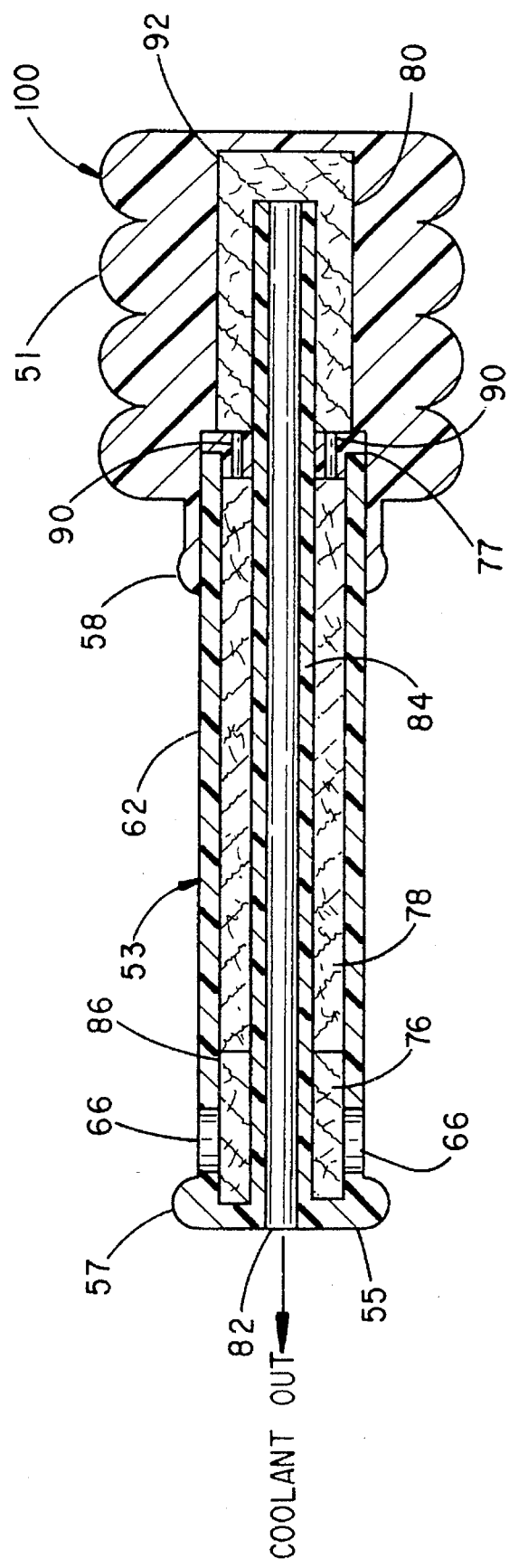
FIG. 6 is a longitudinal cross section view through an alternative disinfectant cartridge useable with the manifolds of the invention.

Returning attention to FIGS. 1, 2 and 4 to 6 views are shown of alternative disinfectant cartridges 50 and 100. FIGS. 4 and 5 depict longitudinal cross section and plan views of a preferred disinfectant cartridge 50. FIG. 6 depicts an alternative cartridge construction 100. With attention first to FIG. 6, the cartridge 100 is principally comprised of a handgrip 51, a tubular body 53 and end cap 55. Multiple seals 57, 58 project as integral annular surfaces from the end cap 55 and handgrip 51. The seals 57, 58 retain the cartridge 100 to the manifold 48 and direct liquid flow within the bore space 52. The seals 57, 58 particularly direct water admitted at the port 54 within a channelway or space 60 defined between an external surface 62 of the body 53 and an interior wall 64 of the bore space 52.

Upon being admitted to the channel space 60, water is directed to a plurality of ports 66 which radially project through the body 53. As water is admitted through the ports 66, the water is directed through an outer bore 86 which contains a series of beds of halogen disinfectant and halogen residual scavenger media 78 and 80 and spacers 76, 77 before being re-directed through a center bore 82 and to the outlet port 56. The bore 82 is provided within an integral, tubular extension piece 84 that extends from a center region of the end cap 55, and which is concentrically positioned within the bore 86.

The handgrip 51, body 53, and end cap 55 are molded as separate, unitary, integral structures from various non-reactive, resilient materials, such as elastomers, polyethylenes and the like. Selected assemblies of such materials may be impregnated with other materials, for example, materials which prevent leeching of the disinfectant by the scavenger media. Preferably, the material used to construct the handgrip 51 and body 53 should accommodate sonic welding and/or adhesive bonding to assure retention of one to the other. The seals 57 and 58 therefore possess sufficient resilience to compress upon mounting the cartridge 100 to the manifold 48.

The nominal dimensions of the seals 57 and 58 are selected to assure a liquid tight seal with the manifold 48 and to retain the cartridge 100 to the adaptor 2. Cartridge retention can be further facilitated by including additional sealing surfaces, such as the seals 57, 58 or other mechanical fasteners referenced below. Separate O'ring seals may be provided in lieu of the integral seals 57, 58.

The spacers 76, 77 comprise porous annular disks and retain the disinfectant media 78 within the bore 86 and the scavenger media 80 within the hand grip 51. The spacers are typically constructed from a variety of fibrous materials and/or porous polymers. Each is configured to an annular shape to mount within the cavity 86 and exhibits a suitable porosity to pass the coolant water and filter undesired contaminants. A number of longitudinal bores 90 are radially positioned about the spacer 77 to further facilitate liquid flow into the scavenger media 80.

The disinfectant media 78 presently comprises a multi-valent iodine resin. Other exemplary disinfectants might comprise a multi-valent iodine resin with bromide, a bromide derivative particulate, quaternary ammonium-silver-chlorine-bromine-bromide bearing medias, other halogen resins or halogen derivatives. The media is provided in sufficient volume to accommodate a useful cartridge life on the order of 5 gallons of water. The volume of media 78 may be varied and/or the type of disinfectant or mixtures of multiple disinfectants to devitalize anticipated types of microbes.

The scavenger media 80 comprises a cast or loose granular porous carbon material, which exhibits a nominal porosity of 0.3 to 10.0 microns. The media 80 mounts within a cavity 92 formed into the hand grip 51. The media 80 removes any iodine taste imparted by the disinfectant 78 to the water and any residual iodine or iodide which might otherwise become entrapped into the liquid. Presently considered scavenger materials are, for example, fine mesh GAC, silver composites, starch, anion resins, cation resins and other halogen scavenger media.

As presently constructed, the cartridge 100 exhibits a nominal, total length in the range of 1½ to 2½ inches and a body length between the seals 57 and 58 in the range of ½ to 1½ inches. The diameter of the seals 57, 58 are sized in a range of 0.18 to 0.500 inches. Such dimensions permit a nominal volume of 0.3 to 1.5 ml of disinfectant within the cartridge 100.

Turning attention next to FIGS. 4 and 5, the presently preferred cartridge 50 is depicted. The cartridge 50 is constructed to nominal dimensions comparable to the cartridge 100, although exhibits a distinguishable arrangement of disinfectant and halogen scavenger media 102 and 104 within a bore 106 of a tubular body 108. A multi-valent, iodine resin serves as the disinfectant media 104. A resin based, silver composite comprises the halogen scavenger media 102. Various singular types or mixtures of disinfectant and halogen scavenger media may be included in granular, resin or cast form at the media beds 102, 104.

A hand grip 110 projects from one end of the body 108 and is integrally formed with the body 108. A number of ribs 111 protrude from the grip 110 to facilitate gripping by the fingers.

A series of annular grooves 112, 114 and 116 are formed into the body 108 to receive a number of O-ring seals 118. Like the seals 57, 58, the seals 118 contain liquid flow within the bore space 52 and the channel space 60 formed between an external surface 120 of the body 108 and the bore wall 64. Liquid flow is particularly directed to one or more inlet ports 122. The ports 122 radially extend through the body 108 into the bore 106, adjacent the hand grip 110.

Upon entering the bore 106, liquid is directed to a head space 127 and then through a number of porous spacers 124, 126 and 128, which are sequentially arranged to separate and retain the beds of disinfectant and scavenger media 102 and 104. The spacers 124, 126 and 128 are adhesively bonded, press fit or sonically welded to the body 108. The spacer 126 may be impregnated with a powdered activated carbon, carbon composite or other material which prevents leeching of the disinfectant 102 by the scavenger media 104 over prolonged storage and/or exposure to heat.

The cartridge 50 is nominally sized to provide a bore 106 having a diameter in the range of 0.175 to 0.500 inches and a length in the range of 0.75 to 2.0 inches. Such a cavity space accommodates a total volume of bactericide in the range of 0.3 to 1.5 ml and a nominal useful cartridge life on the order of 5 gallons of water.

Although the seals can retain the cartridge 50 to the manifold 48, a pair of protrusions 81 also extend from the handgrip 110 to interlock with a pair of mating channels 83 (only one of which shown) at the manifold 48, reference FIG. 2. Upon fitting the protrusions 81 to the channels 83 and twisting the hand grip 110, the cartridge 50 is securely retained to the manifold 48.

Figure 7:
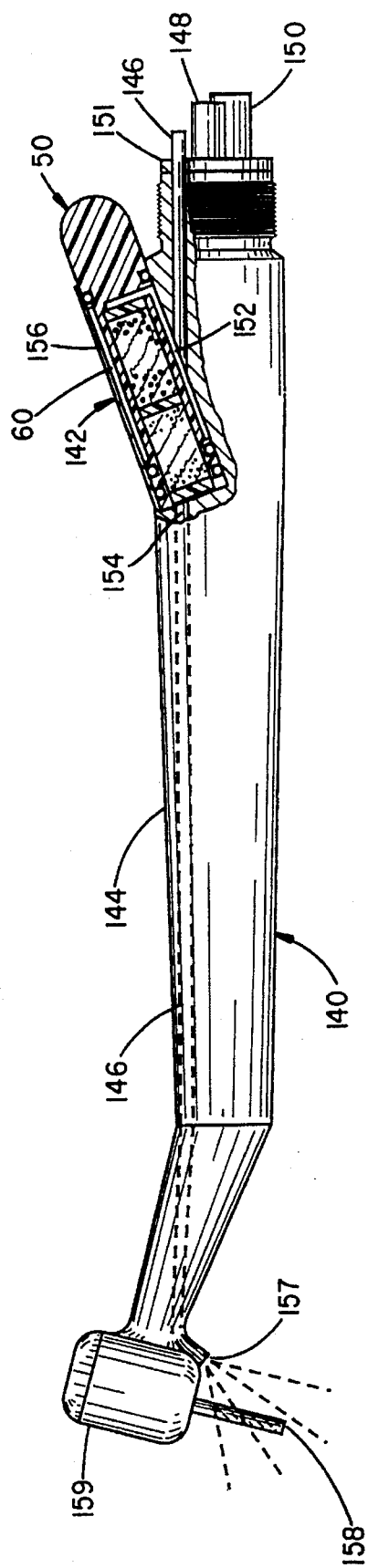
FIG. 7 is a plan view shown in partial longitudinal cross section through a high speed handpiece and wherein the handle includes an integral, disinfectant cartridge manifold.

Appreciating the potential extension of the adaptor 2 into a hand tool, attention is directed to FIG. 7. FIG. 7 depicts a handpiece 140 in partial longitudinal cross section. The handpiece 140 is formed to include a manifold 142 that is integrally cast into a handle 144. Either of the cartridges 50 or 100 can mount to the manifold 142 in the manner described above. A coolant conduit 146, drive air conduit 148 and exhaust air conduit 150 project from a sealed end cap 151. Liquid flow is directed from inlet and outlet ports 152 and 154, along the conduit 146, to a cavity space 156 at the manifold 142. Within the cavity 156, the liquid is directed through the cartridge 50, out the port 154 to a discharge port 157, positioned adjacent a burr 158 at a drive head 159.

The handpiece 140 is essentially the same in all functional respects as the handpiece 4, except the handpiece 140 integrates the adaptor 2 into the handle 144. As with the adaptor 2, the manifold 142 projects from a longitudinal center axis of the handle 144 at an angle in the range of 15 to 45 degrees. The manifold 142 extends from an upper surface of the handle 144 and is positioned to not obstruct normal manipulation and use of the handpiece 140 or potential dislodgement of the disinfectant cartridge 50. The manifold 142 is also positioned to avoid obstruction of room light or the practitioner's view of the work area. Depending upon the construction of the handpiece 140 and the number and positioning of the various conduits 146, 148, 150 or others, the positioning of the manifold 142 may be varied.

Figure 8:
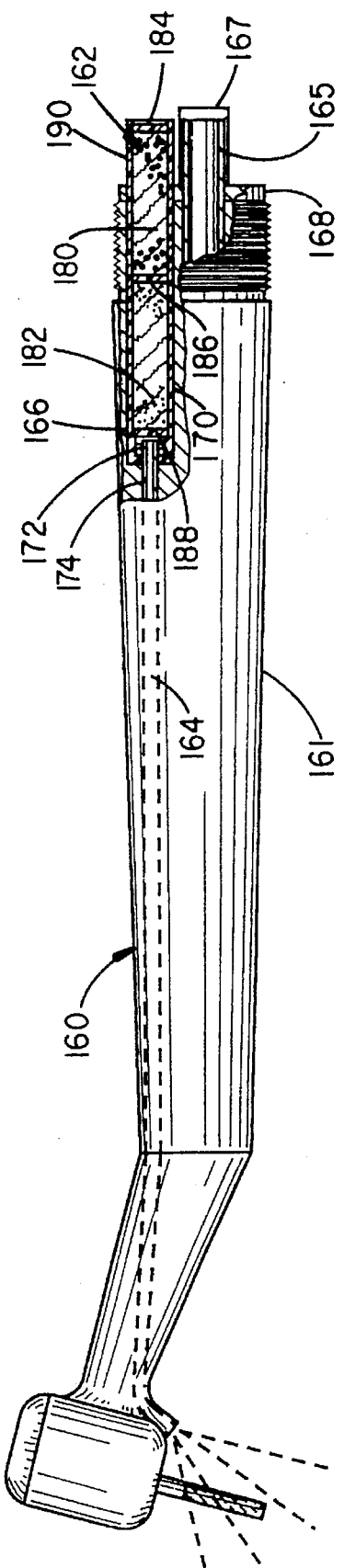
FIG. 8 is a plan view shown in partial longitudinal cross section view through a handpiece including a coaxial disinfectant cartridge manifold.

In that regard, FIG. 8 depicts yet another handpiece 160, which is shown in partial longitudinal cross section. The handpiece 160 includes a disinfectant cartridge 162 that coaxially aligns with a coolant supply conduit 164. The cartridge 162 mounts within a tubular cavity 166 at a handle 161 and extends through a sealed end cap 168. An aperture at the end cap 168 seals about the external surface 170 of the cartridge 162 and aligns the cartridge 162 to the internal conduit 164. An annular seal 172 at a fore-end of the cartridge 162 mounts to a tubular stub piece 174 of the handle 161 to retain the cartridge 162 to the handle 161 and provide a liquid tight seal.

An external water supply conduit can mount directly over the exposed end of the cartridge 162. Adjoining extension pieces 165 and 167 couple to internal supply air and exhaust conduits (not shown).

Liquid flow is directed through a pair of disinfectant and halogen scavenger media beds 180, 182. The beds 180, 182 are separated by porous spacers 184, 186 and 188. The spacers are appropriately secured to the walls of the cartridge housing 190. The media 180 typically comprises a multi-valent iodine resin, and the media 182 typically comprises a halogen scavenger media. The porosity of the media 180, 182 and spacers 184, 186 and 188 are configured to provide a suitable liquid flow characteristic at the handpiece 160, yet obtain a desired devitalization of any admitted microbes.

Figure 9:
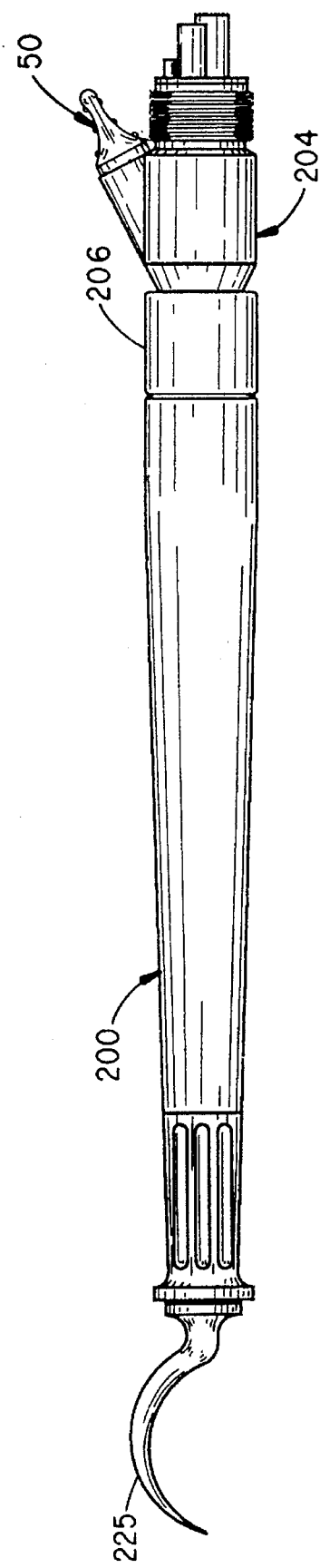
FIG. 9 is a drawing of an air driven sonic scaler including a disinfectant cartridge adaptor.
Figure 10:
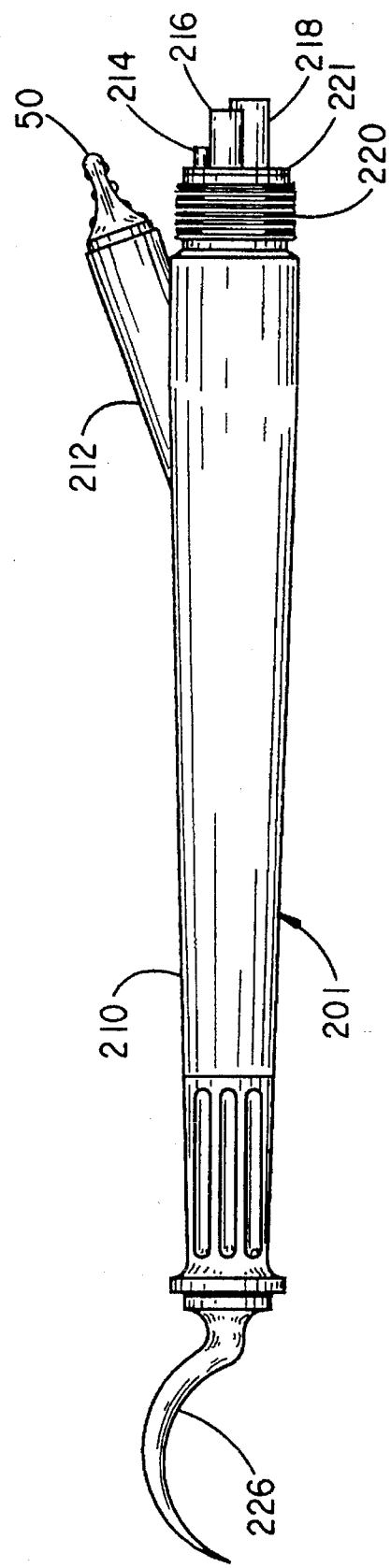
FIG. 10 is a drawing of an air driven sonic scaler including an integral disinfectant cartridge housing.
Figure 11:
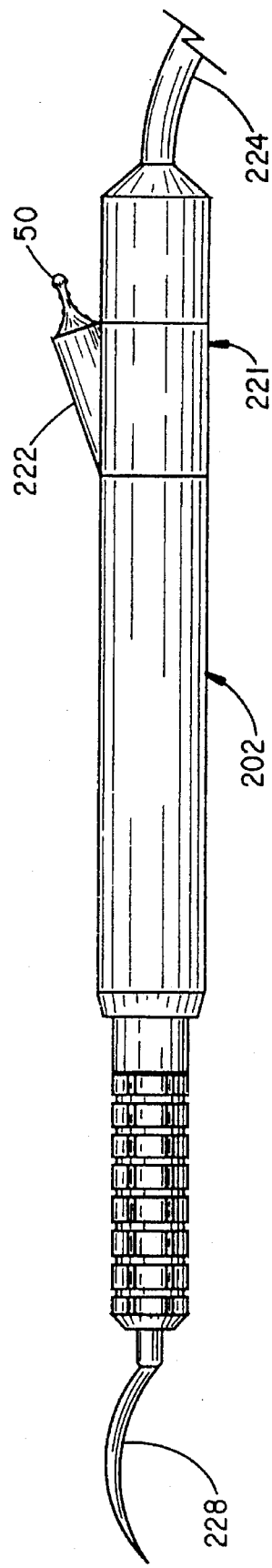
FIG. 11 is a drawing of an electric ultra-sonic scaler including a detachable adaptor and disinfectant cartridge.

FIGS. 9, 10 and 11 depict alternative "sonic" scalers 200, 201 and 202 which are adapted to include the present invention. The scaler 200 includes an adaptor 204 having a threaded coupler 206. The adaptor 204 couples to the scaler 200 in a fashion comparable to the coupler 24 to the adaptor 2. A disinfectant cartridge 50 is secured to the adaptor 204, alternatively the cartridge 100 can be used with the adaptor 204. Because, too, dental scalers do not typically require as many internal conduits as the handpieces 4, such as for fiber optic illumination, it is anticipated the adaptor 204 can be more readily integrated into a typical scaler.

FIG. 10 depicts a scaler 201 having an integral manifold 212. The scaler 201 includes a handle 210 and from which the manifold 212 projects. A disinfectant cartridge 50 is secured to the manifold 212. A water supply conduit 214 and respective supply and exhaust air conduits 216 and 218 project from a threaded end piece 220 and sealed end cap 221.

FIG. 11 depicts an electric or ultra-sonic scaler 202. The scaler 202 includes a detachable adaptor 221 having a manifold 222 that supports a disinfectant cartridge 50. Power and coolant liquid are coupled to the scaler 202 through a supply line 224. Appropriately shaped tool heads 225, 226 and 228 are fitted in conventional fashion to the scalers 200, 201 and 202.

FIGS. 12 through 16 depict yet other adaptations of the invention to dental hand tools. FIG. 12 depicts an air-water syringe or "triplex" syringe 230 which has been adapted to include an integral cartridge manifold 232 at a handle 234. A disinfectant cartridge 50 projects from the manifold 232. A threaded supply line coupler 236 is fitted to the end of the handle 234. Air and water supply conduits 238 and 240 extend from the coupler 236 in conventional fashion. A head piece 242 contains a selector valve assembly 244, which appropriately directs either air, water or a mixture of air and water from a spray tip 245 and separate air and water discharge ports 246 and 248.

Although the syringe 230 has been adapted to include an integral manifold 232, it is to be appreciated the adaptor 2 described at FIG. 2 can be readily mounted to the threaded inlet ends of most commercially available air-water syringes. A microbe free supply of water is thereby obtained from dental syringes.

Figure 13:
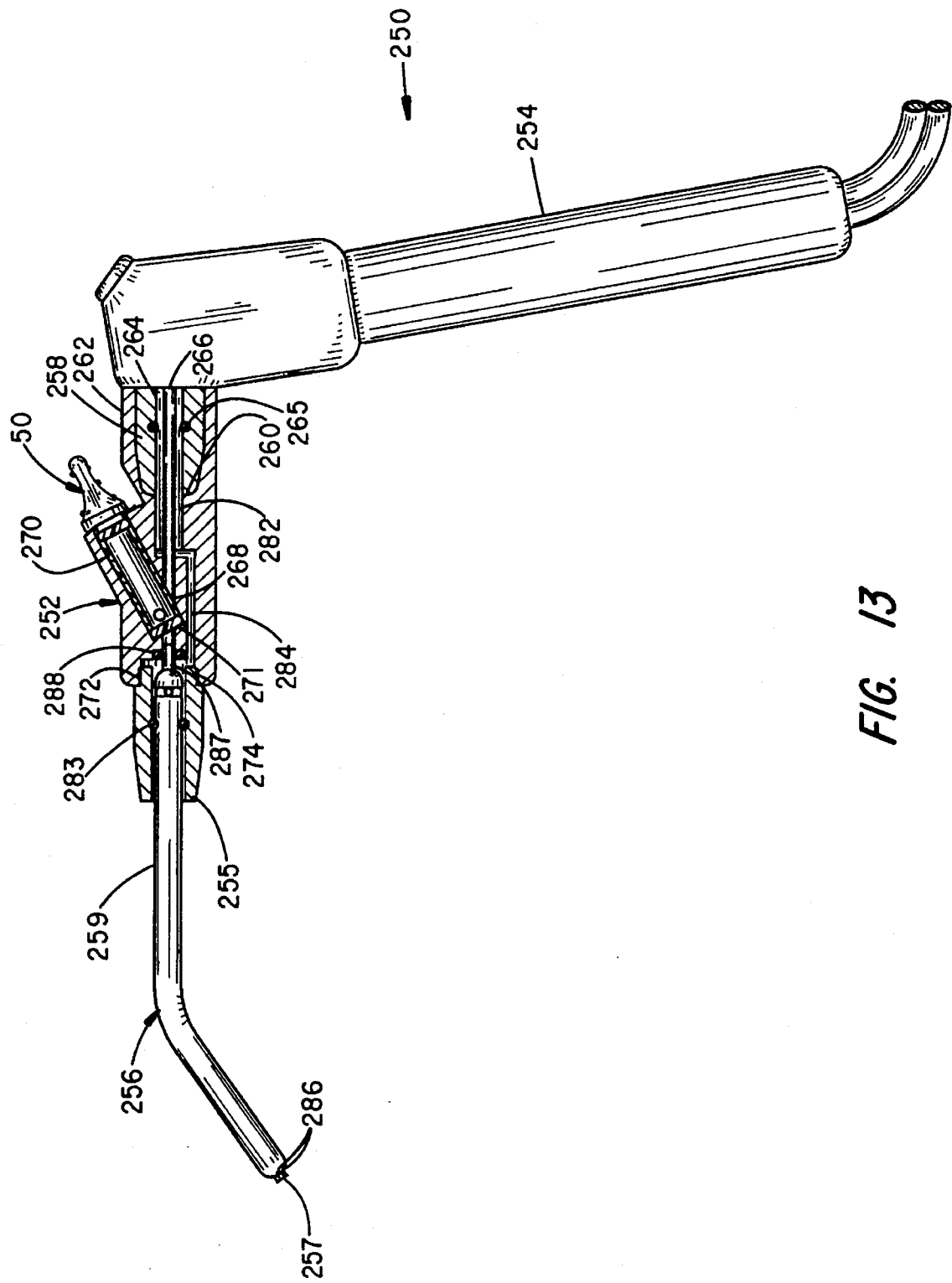
FIG. 13 is a plan view shown in partial longitudinal cross section of an air-water syringe including a sterilizable purification tip.

Other alternative constructions of disinfectant cartridge adaptors useable with air-water syringes are shown at FIGS. 13 through 16. FIG. 13 depicts a syringe 250 which supports an adaptor assembly 252 intermediate a handle 254 and a spray tip 256. The handle 254 is of conventional construction and includes a removeable nut 258. The adaptor 252 includes a housing 262 which mounts over and is secured in the same fashion as a standard tip.

A nozzle piece 264 projects from the housing 262, mounts in the bore 260 and mates with seals 265 contained in conventional fashion beneath the nut 258. The nozzle piece 264 includes a liquid flow bore 266 which opens to an inlet port 268 at a manifold cavity space 270. An outlet port 271 directs liquid from the cartridge 50 to the spray tip 256 and a liquid discharge port 257.

The tip 256 is assembled in conventional fashion. The tip includes a nut 255 which has a threaded surface 272 that interlocks with threads 274 at the adaptor 252. An O'ring seal 283 mounts about a nozzle piece 259 within the nut 255. A stub portion 287 of the nozzle 259 projects into the housing 262 and is sealed at an O'ring seal 288.

Air flow is separately directed from a channel 282, that aligns to ports (not shown) at the handle 254 and an extension channel 284 in the adaptor 252. The channel 284 aligns with a channel (not shown) in the nozzle 259 to separately direct the air to air discharge ports 286 in the tip 256.

A particular advantage of adapting the coupler 252 to use with a tip 256 is that the tips 256 and adaptor 252 can be separately autoclaved. Most dentists also maintain a large supply of tips 256 and as a normal practice change the tips with each patient. The adaptor 252 can thus be readily introduced into the practitioner's normal practice routine as it pertains to infection control. The ability to use a disinfectant cartridge 50 and separately autoclave the adaptor 252 and tip 256 assures a microbe-free supply of water with each use of the syringe 250 for each new patient.

Figure 14:
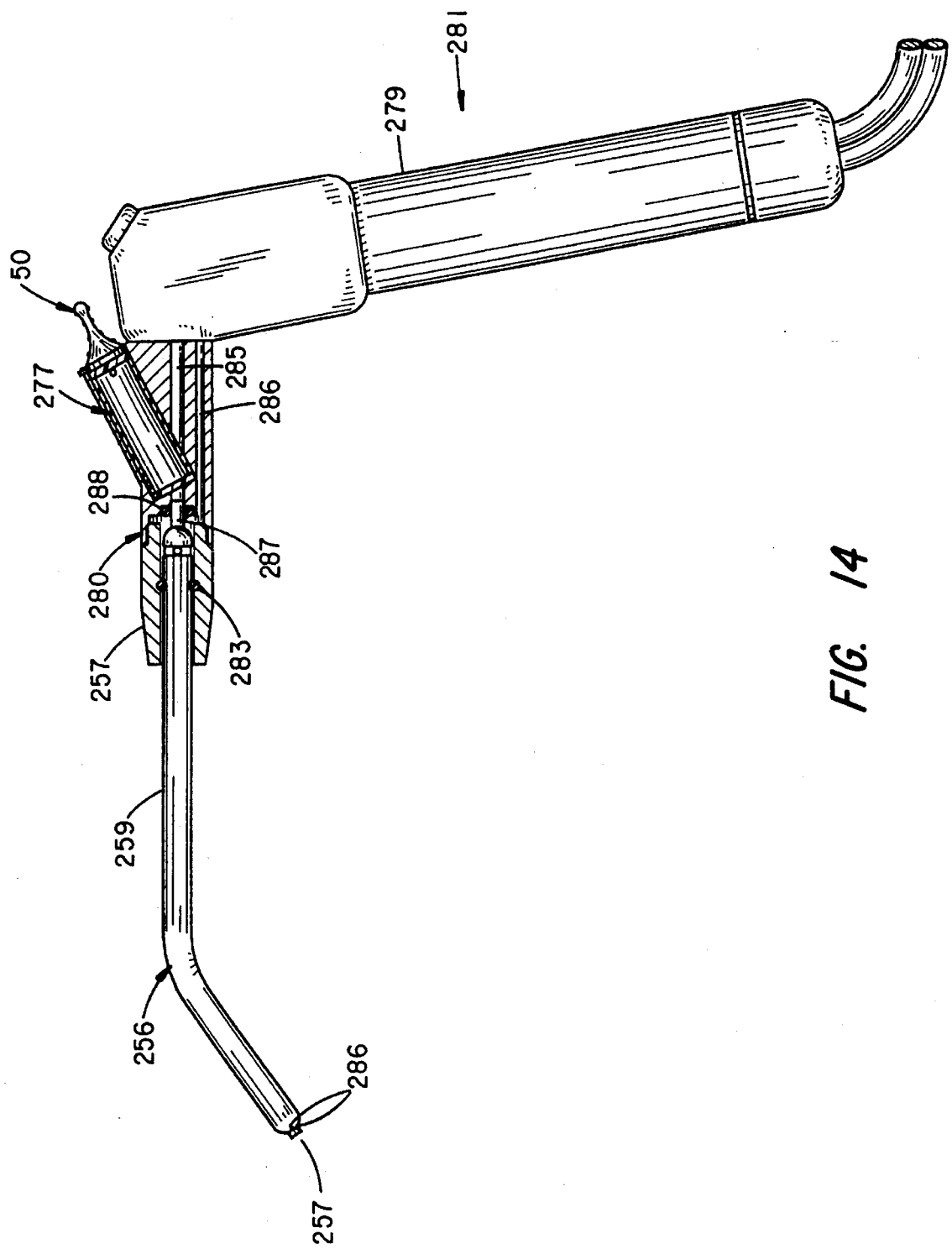
FIG. 14 is a plan view shown in partial longitudinal cross section of an alternative sterilizable purification tip for an air-water syringe.

FIG. 14 depicts another adaptor 280 which can be used with the autoclavable tip 256. The adaptor 280 includes a manifold 277 which supports a cartridge 50. A threaded surface (not shown) extends from the adaptor 280 to mate with an autoclavable handle 279 at a syringe 281. The tip 256 is secured to the adaptor 280 and O'rings 283 seal about the nozzle 259. Water and air conduits (not shown) at the handle 279 align with a liquid conduit 285 and an air conduit 286 in the adaptor 280. A stub extension 287 at the nozzle 259 mounts through an annular seal 288 at the adaptor 280 to isolate liquid flow from the syringe handle 279 through the conduit 285 from air flow through the conduit 286.

Figure 15:
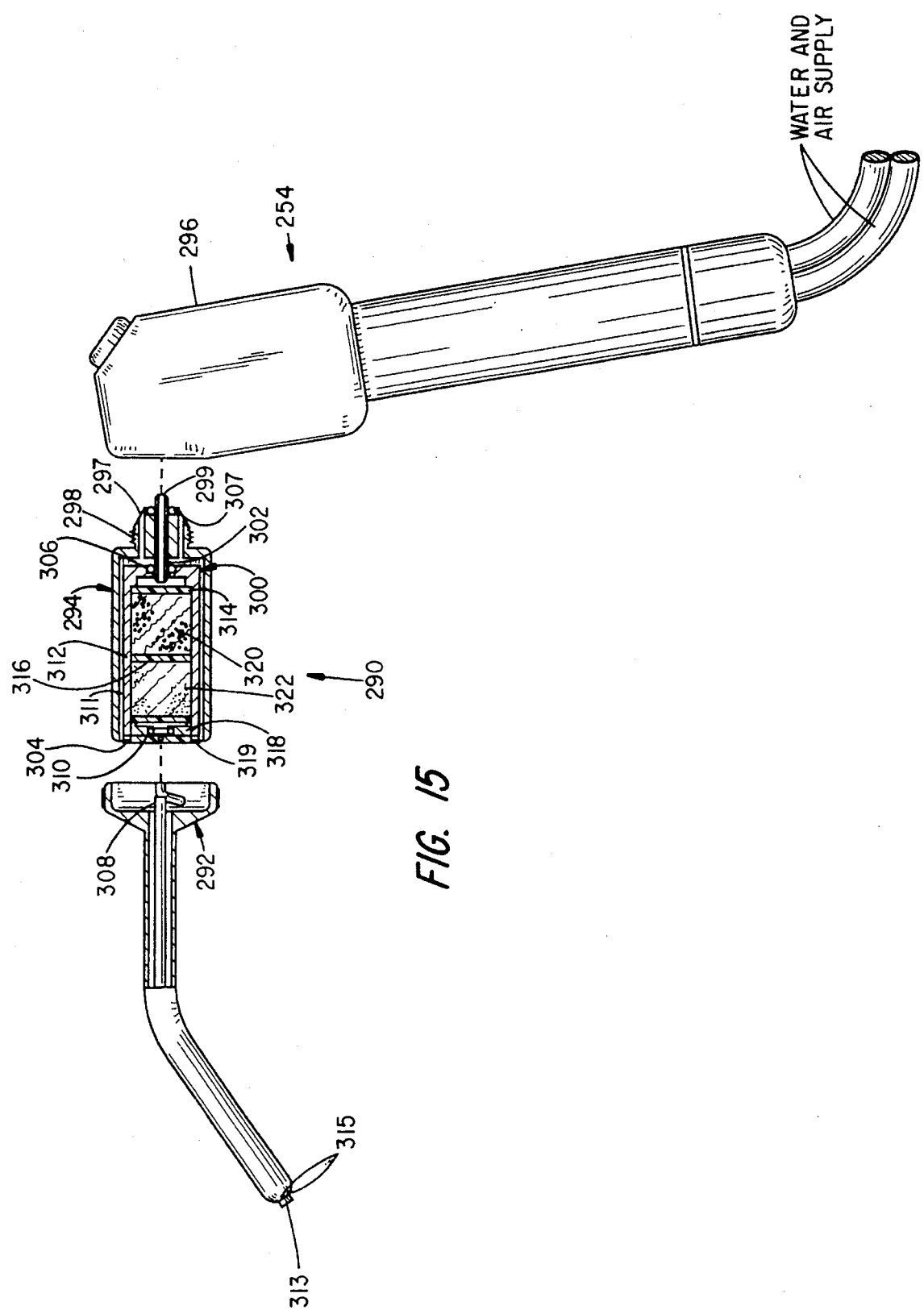
FIG. 15 is a plan view shown in exploded assembly and partial longitudinal cross section of a disinfectant cartridge containing tip which segregates water and air flow for an air-water syringe.

FIG. 15 depicts another conventional air-water syringe 254 and to which a detachable spray tip 290 is shown in exploded assembly and partial longitudinal cross section. The tip 290 includes a nozzle cap 292 which mounts to a cartridge chamber 294. The chamber 294 supports a disposable treatment cartridge 300. The cap 292 seals to the chamber 294 and the chamber 294 mounts to a syringe handle 296 in conventional fashion at a threaded surface 298. Air and water conduits at the handle 296 (not shown), align to an air channel 297 and a liquid channel 299 at the chamber 294.

The cartridge 300 contains disinfectant and halogen scavenger media and mounts within the chamber 294. A stub piece 302 having a bore 299 extends into a cavity space 304 of the chamber 294 and mates with an annular end seal 306 at the cartridge 300. An annular seal 307 at the opposite end of the stub piece 302 mates to the handle 296. Upon securing the chamber 294 to the handle 296, the seals 306 and 307 isolate flow through the air and water channels.

The isolation of the air and water is maintained at the chamber 294 upon attaching the nozzle cap 292. The cap 292 concentrically retains the cartridge 300 to the cap 292 at a bored projection 308. The projection 308 mounts within an annular seal 310 at an outlet end of the cartridge 300. Liquid flow is thereby constrained to flow through the cartridge 300 and be discharged at a liquid discharge port 313.

Air flow is directed around the exterior of the cartridge 300 via voids 319 in an end surface 304 of the body 312. The voids 319 align to the air channel 311 and permit air flow to a channel 321 in the cap 292 after attaching the nozzle cap 292 to the chamber 294. The air is discharged at discharge ports 315.

The cartridge 300 includes a cylindrical body 312 which supports a series of porous spacers 314, 316 and 318. Disinfectant and halogen scavenger media 320 and 322 are positioned between the spacers 314, 316 and 318. The disinfectant media 320 may comprise a multi-valent iodine resin and the scavenger media 322 may comprise a silver-carbon resin. The cartridge is sized to contain a nominal quantity of total bactericide in the range of 0.3 to 1.5 ml, which supports a nominal flow volume of 5 gallons of water. The cartridge exhibits a diameter in the range of 0.18 to 0.50 inches and a total length of 0.75 to 2.0 inches.

Figure 16:
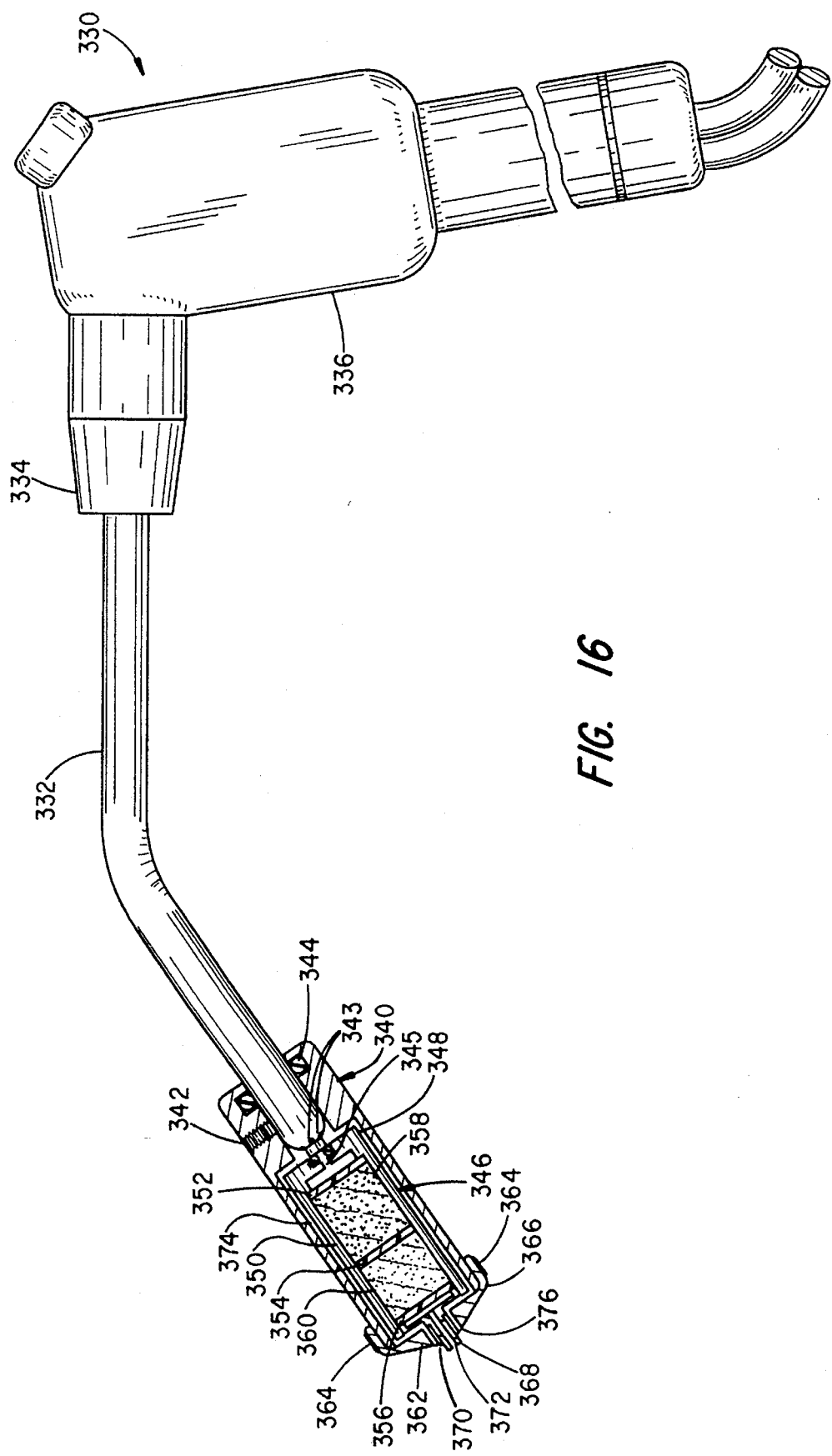
FIG. 16 is a plan view shown in partial longitudinal cross section of a disinfectant cartridge adaptor which mounts to the tip of an air-water syringe and which segregates water and air flow.

FIG. 16 depicts yet another air-water syringe assembly 330 which includes a detachable spray tip 332. The tip 332 is of conventional construction and mounts in conventional fashion to a nut 334 at a handle 336.

Secured to the discharge end of the tip 332 is a cartridge chamber 340. The chamber 340 is retained to the tip 332 with a set-screw 342 or other suitable retainer. An annular seal 344 provides an air tight connection to the tip 332. Air and liquid discharge ports 343 and 345 are appropriately isolated upon securing a disinfectant cartridge 346 to the chamber 340. A cavity space 348 within the chamber 340 receives the cartridge 346.

The cartridge 346 includes a cylindrical body 350 which supports a number of porous spacers 352, 354 and 356 to seal quantities of disinfectant and halogen scavenger media 358, 360 within the body 350. The disinfectant media 358 may comprise a quantity of a multi-valent iodine resin and the halogen scavenger may comprise a silver based composite media.

A cover 362 mounts to a fore end of the chamber 340 at a pair of projections 364. The projections 364 align with slotted grooves 366 cut into the cover 362 such that, upon mounting the cover 362 to the projections 364 and rotating the cover 362, the cover 362 is retained to the chamber 340. Simultaneously, a bored projection 368 of the spacer 356 mounts through an orifice 370 in the cover 362 and provides a liquid discharge port 372. Air, in turn, is directed from the ports 343 to a channel 374 and out an orifice 376 that surrounds the orifice 370.

Although a pair of media beds are depicted for the disclosed cartridges, the disinfectant and halogen scavenger media may comprise a single media bed containing singular concentrations of any of the noted materials or mixtures of the materials. On occasion and depending upon the available water supply, it may be desired to use a cartridge which contains only a hologen disinfectant or a halogen scavenger media. Various other sequential bed arrangements of the same or other materials may also be provided. Other materials, such as a blocker material which prevents disinfectant leeching may be mounted intermediate the disinfectant and scavenger media.

Recalling that the air passing through the adaptors and hand tools discussed above may also contain undesired microbial contaminants, FIGS. 18 through 22 depict assemblies that have been adapted to separately treat the air and water flow. FIG. 18 depicts an end view of an adaptor 380 of substantially similar construction to the adaptor 2, except that a pair of cartridge receiving manifolds 382 and 384 acutely project from the body 386. The manifold 382 is aligned to interrupt a liquid conduit 388 and the manifold 384 is aligned to interrupt an air conduit 390 in the body 386. An exhaust air conduit 392 and optical fiber 394 also project from the adaptor body 386.

Disinfectant cartridges (not shown), but similar to the cartridges 50 and 100, separately mount to the manifolds 382, 384. Identical cartridges can be provided at each manifold. Alternatively, appreciating the differences in the flow characteristics of air, the concentrations, types and arrangement of the disinfectant media within the air cartridge may necessarily be tailored to optimize treatment efficiency for common airborne contaminants.

FIG. 19 depicts another adaptor 400 having a threaded coupler 402 and a body 404. A pair of water and air treatment cartridges 406, 408 are coaxially supported within a pair of cavities 410 and 412. The cartridges 406, 408 mount through a bore 411 of the coupler 402 and align to liquid and air supply conduits 414, 416. An exhaust air conduit 418 and optical fiber 420 also extend from the adaptor 400. Annular seals 422 are provided at the inlet and outlet ends of each of the cartridges 406, 408 and isolate flow, upon securing the adaptor to a hand tool.

Each cartridge 406, 408 contains a pair of treatment media beds 424, 426 and 428, 430. At least one of the beds at each cartridge includes a disinfectant. Although the air cartridge shows a pair of media beds 428, 430, a single disinfectant bed may be provided.

FIG. 20 depicts a handpiece 440 that has been adapted in a fashion similar to the handpiece 160 to receive a pair of air and water cartridges 442 and 444. The cartridges 442, 444 are retained at separate flow cavities 446, 448 which align to water and air conduits 450, 452. The cartridges 442, 444 project from an end seal 454. Mating bores of an air/water supply conduit mount to the exposed ends of the cartridges 442, 444.

Although FIGS. 18 and 20 depict separate air and water cartridges, it is to be appreciated that a single cartridge containing segregated air and water flow channels might be mounted to an adaptor or hand tool. In this regard, FIGS. 21 and 22 respectively depict longitudinal section and cross section views through a cartridge adaptor assembly 460. The assembly 460 is of a comparable construction to the adaptor 2, although is arranged to support a single cartridge 462 which contains separate flow columns 461, 463 for the water and air within a single cartridge body 464. A cartridge manifold 466 includes a cavity 468 that receives the cartridge 462.

As seen at FIG. 22, the manifold 466 is laterally offset from the vertical center of the adaptor 460 to align with separate liquid and air conduits 470, 472. The conduits 470, 472, are bored within an adaptor body 474. Stub pieces 476, 478, 480, 482 extend from the body 474 and mate to appropriate supply conduits (not shown). The outlet end of the adaptor 460 is fitted with a threaded coupler 484 in a fashion similar to that of the coupler 24. Press fit into the base of the cavity 468 are a pair of stub pieces 486, 488 that align to continuations 471, 473 of the conduits 470, 472.

The cartridge body 464 is formed to include a number of annular recesses 489 which support a number of O'ring seals 490. The seals 490 isolate the exterior surface of the cartridge 460 into a pair of regions 492, 494. The air and water flow through the conduits 472, 470 is interrupted at the regions 492, 494 and directed to provided ports 496, 498.

Upon entering the body 464, the air and water are directed to the separate flow columns 461, 463 which are separated at a center baffle 500. As water enters the port 494, the water is directed from a head space 495 through a pair of media beds 502, 504, which are separated by a number of half moon spacers 506. From the bed 504, the water is directed to the stub piece 486. O'ring seals 508 separately seal the stub pieces 486, 488.

Air flow is directed from the inlet port 496 along an internal channel 510 to a head space 512. The air is redirected at the head space through a single media bed 514 and half-moon, end spacers 506 to the stub piece 488. The adaptor 460 thus provides a single cartridge 462 which is able to purify both of the supplied air and water prior to discharge from a supported hand tool (not shown).

Appreciating the offset mounting of the cavity 468, it is also necessary that the cartridge 462 actively interlock with the manifold 466. A resilient pin 516 is provided to this end. The pin 516 also aligns the cartridge 462 to the manifold 466 and the stub pieces 486, 488. The pin 516 projects from the cartridge 460 and mates with a bore 518 at the manifold 466. Cartridge release is effected by depressing the pin 516, while pulling on a handgrip 520. A positive attachment is thereby obtained which assures that the cartridge 462 is not inadvertently ejected, such as in the event of a blocked air passage.

Although FIGS. 18 through 22 depict adaptors and hand tools of comparable organizations to the assemblies of FIGS. 1 through 16, still other arrangements are possible. Preferably any arrangement should accommodate one or more disposable air and water treatment cartridges and be compatible with existing hand tools without adding undue bulk. The assemblies should also permit placement of the cartridges as physically close as possible to the air and water discharge ports of the hand tool to assure the delivery of microbe free air and water. Desirably any arrangement should also be constructed to accommodate cost efficient manufacturing practices.

While the invention has been described with respect to various presently considered constructions and various alternative modifications and improvements thereto, still other constructions may be suggested to those skilled in the art. The following claims should therefore be interpreted to include all equivalent constructions within the spirit and scope thereof.

What is claimed is:

1. Disinfectant apparatus comprising:

a) an adaptor housing including a plurality of flow bores, means mountable to a dental hand tool for coupling said flow bores to mating conduits of the hand tool at an outlet end of said housing and to air and water supply conduits at an inlet end to said housing, and wherein a manifold cavity interrupts at least one of said flow bores which conveys water;

b) cartridge means having inlet and outlet ports for containing a halogen disinfectant media; and c) means for non-permanently sealing said cartridge means within the manifold cavity in flow communication with the water conveying one of said flow bores to convey water through said inlet and outlet ports, whereby water is directed through said cartridge and purified prior to discharge from said hand tool.

2. Apparatus as set forth in claim 1 wherein said cartridge means includes a scavenging media which removes residuals of said disinfectant media from the water.

3. Apparatus as set forth in claim 2 wherein said housing includes a threaded annular coupler, wherein an annular ring secures said coupler to a first groove in said housing, and wherein said coupler includes a second groove for retaining said ring.

4. Apparatus as set forth in claim 2 wherein said housing includes a plurality of stub conduits which extend from said flow bores, and wherein said housing includes a threaded surface concentric to said stub conduits which surface mounts to a threaded coupler which supports said air and water supply conduits.

5. Apparatus as set forth in claim 2 wherein said cartridge means includes means for blocking the leeching of the disinfectant by said scavenging media.

6. Apparatus as set forth in claim 5 wherein the blocking means comprises a spacer impregnated with activated carbon.

7. Apparatus as set forth in claim 1 including means for interlocking said cartridge to said housing.

8. Apparatus as set forth in claim 7 wherein a protrusion at a cartridge body interlocks with a channel at said adaptor housing.

9. Apparatus as set forth in claim 1 wherein said cartridge means includes a tubular body having a longitudinal bore, wherein said bore contains said disinfectant media, wherein said bore terminates at one end at said outlet port, wherein said inlet port transversely projects through the cartridge body and communicates with the longitudinal bore, and further including a plurality of annular seals mounted to the cartridge body such that a flow channel communicating with said inlet port is defined within the manifold cavity upon securing the cartridge means thereto.

10. Apparatus as set forth in claim 9 wherein the cartridge means includes a handgrip, and wherein a protrusion at the cartridge body interlocks with a channel at the adaptor housing, whereby the cartridge means is retained to the adaptor housing.

11. Apparatus as set forth in claim 10 wherein said handgrip includes a region which defines one of said annular seals.

12. Apparatus as set forth in claim 9 wherein an end cap to the tubular body includes a seal and further includes a tubular projection having a bore, wherein said projection mounts within the longitudinal bore of said tubular body and wherein a disinfectant scavenger media is retained within said bore.

13. Apparatus as set forth in claim 9 wherein the cartridge body includes a plurality of annular grooves which receive a plurality of O'ring seals, and wherein the longitudinal bore includes a multi-valent iodine disinfectant media and a halogen scavenger media which removes free iodide ions.

14. Apparatus as set forth in claim 1 wherein the cartridge means includes a plurality of spacers arranged within a longitudinal bore to separate first and second treatment media, wherein said first treatment media comprises a multi-valent iodine disinfectant, wherein the second treatment media comprises a halogen scavenger media which removes free iodide ions.

15. Apparatus as set forth in claim 14 wherein said first media comprises media selected from a class of media including multi-valent iodine resins, multi-valent iodine resins with bromide, quaternary ammonium-silver-chlorine-bromine-bromide bearing medias and other halogen derivatives and said second media comprises media selected from a class of media including fine mesh GAC, silver composites, starch, anion resins, cation resins and other halogen scavenger media.

16. Apparatus as set forth in claim 1 wherein said adaptor housing includes a threaded annular coupler, wherein an annular ring secures said coupler to a first groove in said housing, and wherein said coupler includes a second groove for retaining said ring.

17. Apparatus as set forth in claim 1 wherein said manifold cavity acutely extends from a longitudinal axis of the adaptor housing in a range of 15 to 45 degrees.

18. Apparatus as set forth in claim 1 wherein said manifold cavity is coaxial with a longitudinal axis of said adaptor housing.

19. Apparatus as set forth in claim 18 wherein said cartridge means comprises a tubular body having a longitudinal bore, wherein said bore includes a multi-valent iodine disinfectant media, a halogen scavenger media, a plurality of porous spacers which separate said disinfectant and scavenger media from one another, first and second end caps containing through apertures, and seal means concentric to said apertures.

20. Apparatus as set forth in claim 1 wherein said manifold cavity interrupts first and second bores which convey water and air, and including means for securing said cartridge means to said adaptor housing in flow communication to at least one of said first and second bores.

21. Apparatus as set forth in claim 1 wherein said cartridge means comprises a tubular body having first and second longitudinal bores, wherein said body includes a plurality of annular seals, wherein at least one of said seals at an outer surface of said body defines a first flow channel at the manifold cavity which communicates water from the water supply conduit to a first aperture in flow communication with said first bore, wherein at least a second of said seals at an outer surface of said body defines a second flow path at the manifold cavity which communicates air from the air supply conduit to a second aperture in flow communication with said second bore, and wherein said first and second bores include a multi-valent iodine disinfectant media.

22. Apparatus as set forth in claim 1 wherein said adaptor housing includes first and second manifold cavities, wherein said first cavity interrupts a bore which conveys water and said second cavity interrupts a bore which conveys air, and wherein first and second cartridge means, each containing a disinfectant media, mount within said first and second bores.

23. Disinfectant apparatus comprising:

a) an adaptor housing including a plurality of flow bores, a coupler which mounts to a hand tool for coupling said flow bores to mating conduits of the hand tool at an outlet end of said housing, and a plurality of stub conduits which extend from said flow bores at an inlet end of said housing, and wherein a manifold cavity acutely extends from a longitudinal axis of the housing and interrupts at least one of said flow bores; and b) a disinfectant cartridge including a tubular body having a longitudinal bore, wherein said bore contains a disinfectant media and a halogen scavenger media, wherein said bore terminates at one end at an outlet port, wherein an inlet port projects through the cartridge body and communicates with the longitudinal bore, and further including a plurality of seals mounted to the cartridge body such that a flow channel is defined within the manifold cavity which communicates with said inlet port upon securing the cartridge thereto.

24. Disinfectant apparatus comprising:

a) a housing including a manifold cavity having an inlet bore to said cavity, an end cap including a discharge port, and means for securing said end cap to said housing;

b) a cartridge mounted within said housing having a tubular body containing a plurality of spacers arranged within a bore to separate first and second treatment media, wherein said first treatment media comprises a disinfectant, and wherein said second treatment media comprises a halogen scavenger which removes residuals of said disinfectant media; and c) means for sealing and retaining said housing and cartridge to a nozzle piece of a dental hand tool in flow communication to a water conveying conduit, whereby purified water is discharged from the discharge port.

25. Apparatus as set forth in claim 24 wherein said first treatment media comprises a multi-valent iodine resin and wherein said second treatment media comprises a silver composite media.

26. Apparatus as set forth in claim 24 wherein said housing includes a set screw for retaining said housing to said nozzle piece.

27. A dental hand tool comprising:

a) a handle including a plurality of flow bores for conveying air and water, means for coupling said flow bores to mating air and water supply conduits, and including a manifold cavity in flow communication with one of said flow bores;

b) a cartridge means having inlet and outlet ports for containing a disinfectant media; and c) means for non-permanently sealing said cartridge means within the manifold cavity in flow communication with the water conveying one of said flow bores to convey water through said inlet and outlet ports, whereby water is directed through said cartridge means and purified prior to discharge from said hand tool.

28. Apparatus as set forth in claim 27 wherein said cavity acutely extends from a longitudinal axis of said handle, and wherein said cartridge means includes a handgrip, whereby said cartridge can be secured to or removed from said handle.

29. Apparatus as set forth in claim 28 wherein said cartridge means includes a tubular body having a longitudinal bore, wherein said bore contains said disinfectant media, wherein said bore terminates at one end at said outlet port, wherein said inlet port projects through the cartridge body and communicates with the longitudinal bore, and further including a plurality of annular seals mounted to the cartridge body such that a flow channel communicating with said inlet port is defined within the manifold cavity upon securing the cartridge means thereto.

30. Apparatus as set forth in claim 27 wherein said cartridge means comprises a tubular body having a longitudinal bore, wherein said bore includes a multi-valent iodine disinfectant media, a halogen scavenger media, a plurality of spacers which separate said disinfectant and scavenger media from one another, first and second end caps containing through apertures, and seal means concentric to said apertures.

31. Apparatus as set forth in claim 27 wherein said cartridge means comprises a tubular body having a longitudinal bore, wherein said bore includes a halogen disinfectant media, a halogen scavenger media, and means for separating said disinfectant and scavenger media from one another and for preventing the leeching of said disinfectant by said scavenger media.

32. Disinfectant apparatus comprising:

a) an adaptor housing including a plurality of flow bores, coupler means for coupling said flow bores to mating conduits of a hand tool at an outlet end of said housing and to air and water supply conduits at an inlet end to said housing, and wherein a manifold cavity interrupts at least one of said flow bores;

b) cartridge means having inlet and outlet ports for containing a treatment material selected from a class of materials containing a halogen disinfectant and a halogen scavenger media; and c) means for non-permanently sealing said cartridge means within the manifold cavity in flow communication with the one of said flow bores, whereby either said water and/or air is directed through said cartridge and purified prior to discharge from said hand tool.

33. Apparatus as set forth in claim 32 wherein said cartridge means includes means for blocking the leeching of the disinfectant by said scavenging media.

\* \* \* \* \*